United States Patent [19]
Ohta et al.

[11] Patent Number: 5,610,309

[45] Date of Patent: Mar. 11, 1997

[54] ELECTROLUMINESCENT DEVICE COMPRISING OXADIAZOLE COMPOUNDS LUMINESCENT MATERIAL, OXADIAZOLE COMPOUNDS FOR THE DEVICE, AND METHOD OF PRODUCING OXADIAZOLE COMPOUNDS

[75] Inventors: Masafumi Ohta, Susono; Yohta Sakon, Numazu; Toshihiko Takahashi, Numazu; Chihaya Adachi, Numazu; Kazukiyo Nagai, Numazu, all of Japan

[73] Assignee: Ricoh Company, Ltd., Tokyo, Japan

[21] Appl. No.: 478,674

[22] Filed: Jun. 7, 1995

Related U.S. Application Data

[62] Division of Ser. No. 321,765, Oct. 12, 1994, which is a division of Ser. No. 51,070, Apr. 14, 1993, Pat. No. 5,420,288.

[30] Foreign Application Priority Data

| Apr. 14, 1992 | [JP] | Japan | 4-121194 |
| Jun. 9, 1992 | [JP] | Japan | 4-174801 |
| Jun. 20, 1992 | [JP] | Japan | 4-186051 |
| Jul. 27, 1992 | [JP] | Japan | 4-219792 |
| Sep. 17, 1992 | [JP] | Japan | 4-273692 |
| Sep. 29, 1992 | [JP] | Japan | 4-284041 |
| Apr. 1, 1993 | [JP] | Japan | 5-098890 |

[51] Int. Cl.$^6$ ............................................. C07D 413/10
[52] U.S. Cl. ........................................ 546/256; 548/145
[58] Field of Search ............................ 548/145; 540/256

[56] References Cited

U.S. PATENT DOCUMENTS

| 3,511,834 | 5/1970 | Siegeist | 548/145 |
| 5,336,546 | 8/1994 | Hironaka | 428/209 |

*Primary Examiner*—Robert Gerstl
*Attorney, Agent, or Firm*—Oblon, Spivak, McClelland, Maier & Neustadt, P.C.

[57] ABSTRACT

An electroluminescent device is composed of a negative electrode, a positive electrode, and an organic compound layer which is interposed between the negative electrode and the positive electrode and includes at least one oxadiazole compound with a plurality of aryl oxadiazole structures. Novel oxadiazole compounds for use in the electroluminescent device and a method of producing the oxadiazole compounds are disclosed.

3 Claims, 12 Drawing Sheets

ELECTROLUMINESCENT DEVICE COMPRISING OXADIAZOLE COMPOUNDS LUMINESCENT MATERIAL, OXADIAZOLE COMPOUNDS FOR THE DEVICE, AND METHOD OF PRODUCING OXADIAZOLE COMPOUNDS

This is a Division of application Ser. No. 08/321,765 pending filed on Oct. 12, 1994, which is a division of application Ser. No. 08/051,070 filed Apr. 14, 1993, now U.S. Pat. No. 5,420,288.

BACKGROUND OF THE INVENTION

1. Field of the Invention

The present invention related to an electro-luminescent device comprising an oxadiazole compound or derivative serving as an electroluminescent material and/or as a charge transporting material, with excellent film-forming properties and electroluminescence with a satisfactorily high luminance.

The present invention relates to novel oxadiazole compounds which are useful not only as organic electroluminescent materials and charge transporting materials, but also as fluorescent brightening agents, and to a method of producing the oxadiazole compounds.

2. Discussion of Background

In recent years, a demand for a planar display device with a smaller power consumption and a smaller space occupation in comparison with a cathode-ray tube (CRT) is increasing in accordance with the diversification of the development of information systems. As such a planar display device, for instance, liquid crystal displays and plasma displays are in general use. However, recently, attention has been paid to electroluminescent devices (EL device) of a light emission type, which are capable of displaying clear images.

The above-mentioned electroluminescent devices can be classified into inorganic electroluminescent devices and organic electroluminescent device, depending upon the electroluminescent material employed therein. Of these, inorganic electroluminescent devices have already been used in practice.

An inorganic electroluminescent device is of a so-called collision and excitation type and is driven and emits light by the collision of electrons accelerated by the application of a high voltage to a luminescent center. Because of the application of high voltage for driving the electroluminescent device, such an inorganic electroluminescent device has the problem that the cost of peripheral equipments therefor are expensive.

In contrast to this, an organic electroluminescent device of an injection luminescence type comprises an organic luminescent layer interposed between positive and negative electrodes, each with a different work function, in which positive holes injected from the positive electrode and electrons injected from the negative electrode are combined in the organic luminescent layer, and a light with the same wavelength as that of the fluorescence of the luminescent layer is emitted. Because of the injection luminescence, the organic electroluminescent device can be driven by the application of a low voltage and can emit a luminescent light with a different color as desired by changing the electroluminescent material employed in the organic luminescent layer.

In addition to the above, the properties of organic compounds employed in the above-mentioned organic electroluminescent device differ, for instance, in accordance with substituent groups contained therein, so that the desired electroluminescent material can be fabricated from organic materials with more freedom in comparison from inorganic materials.

Therefore, it is considered that any electro-luminescent material can be obtained by changing the molecular structure of the organic compound employed, if the conditions of electrons in the molecule are taken into consideration. Theoretically, it is possible to emit lights with any colors including red through blue by use of organic compounds. A variety of electroluminescent materials capable of stably emitting light with a color such as green, yellow or orange are actually proposed.

Conventionally, the following electroluminescent devices with a two-layered structure and electro-luminescent device with a three-layered structure have been reported: a two-layered electroluminescent device with an SH-A structure in which a hole-transporting layer and a luminescent layer are formed between a hole injection electrode and an electron injection electrode (Japanese Laid-Open Patent Application 59-194393 and Appl. Phys. Lett. 51,913 (1987), and a two-layered electroluminescent device with an SH-B structure in which a luminescent layer and an electron-transporting layer are formed between a hole injection layer and an electron injection layer (U.S. Pat. No. 5,085,947, Japanese Laid-Open Patent Application 2-25092, and Appl. Phys. Lett. 55,1489 (1989); and a three-layered electroluminescent device with a DH structure in which a hole-transporting layer, a luminescent layer, and an electron-transporting layer are formed between a hole injection electrode and an electron injection electrode (Appl. Phys. Lett. 57,531 (1990)).

As the material for the above-mentioned hole injection electrode, materials with a large work function such as gold and ITO (indium-tin-oxide) can be employed, and as the material for the electron injection electrode, materials with a small work function such as calcium, magnesium, aluminum, and alloys thereof can be used.

Moreover, varieties of organic compounds have been proposed for use in the hole-transporting layer, luminescent layer and electron transporting layer.

Examples of the above-mentioned organic compounds include aromatic tertiary amines of the hole-transporting layer; aluminum trisoxine (Japanese Laid-Open Patent Applications 59-194393 and 63-295695), styryl amine derivatives, styryl benzene derivatives and the like (Japanese Laid-Open Patent Application 2-209988) for the luminescent layer; and oxadiazole derivatives (Nippon Kagaku Kaishi No. 11, p.1540 (1991)), Japanese Laid-Open Patent Applications 4-212286, 4-308688, 4-363891 and 4-363894) for the electron-transporting layer.

Electroluminescent devices with various structures with an initial luminance of as high as 1000 cd/m$^2$ or more by the application of a drive voltage of about 10 V have been fabricated by use of organic electroluminescent materials. However, when the above-mentioned electro-luminescent devices comprising the conventional organic materials are continuously driven, the luminescent output reduces within several hours and the drive voltage therefor has to be increased.

Thus, the conventional EL devices have a serious problem in the durability when used for an extended period of time.

In particular, suitable luminescent materials for an electroluminescent device for the emission of blue light have not yet been discovered, so that there are many problems to be solved such as the improvement of luminescence efficiency in the blue-light emitting electroluminescent device. In addition to the above, the research and development of a carrier-injection type electro-luminescent device comprising an organic compound as an illuminant have been just started and materials for the electroluminescent device and the application thereof have not sufficiently been studied. As a matter of course, the carrier-injection type electroluminescent device has many problems to be solved such as the improvement of luminance and durability of the device, and the control of the wavelength of the light emitted therefrom.

Varieties of oxadiazole derivatives are conventionally known, and are effectively utilized as the luminescent components for conventional electroluminescent devices. For instance, Japanese Laid-Open Patent Application 3-205479 discloses an electroluminescent device comprising as a luminescent component an oxadiazole derivative, which includes an alkenyl group, a carbazolyl group or an aminophenyl group as a substituent. However, there are some problems in the luminance and film-forming properties of the oxadiazole derivative used in the above electroluminescent device.

As mentioned previously, no luminescent materials which can stably emit blue light with a high luminance have been developed either for inorganic EL devices for organic EL devices.

1,1,4,4-tetraphenyl-1,3-butadiene derivatives and styryl benzene derivatives have been proposed as luminescent materials capable of emitting blue light for use in an organic EL device. However, these materials have no satisfactory film-forming properties, and no satisfactory luminance and stability when used in the electroluminescent devices. Moreover, as an electron-transporting material, 2-(4-tert-butylphenyl)-5-(p-biphenyl)-1,3,4-oxadiazole is disclosed in Japanese Laid-Open Patent Application 2-250292, but this material is easily crystallized and lacks in the stability.

Furthermore, an oxadiazole compound represented by the following formula (A) is disclosed in Japanese Patent Publication 45-2467:

However, the above oxadiazole compound is merely employed as an intermediate for producing stilbene derivatives.

SUMMARY OF THE INVENTION

Accordingly, a first object of the present invention is to provide an electroluminescent device with excellent durability, capable of exhibiting satisfactorily high luminance and luminescent performance for an extended period of time.

A second object of the present invention is to provide a novel oxadiazole compound which can be utilized as an effective component for an electroluminescent device, which exhibits high luminance and stable film-forming properties, serving as a luminescent material for the emission of a blue light with satisfactory luminance with high stability for an extended period of time, or serving as an electron-transporting material having excellent film-forming properties, high luminance and high stability for an extended period of time.

A third object of the present invention is to provide a method of producing the above novel oxadiazole compound.

The first object of the present invention can be attained by an electroluminescent device comprising a negative electrode, a positive electrode, and an organic compound layer which is interposed between the negative electrode and the positive electrode, and comprises at least one oxadiazole compound with a plurality of aryl oxadiazole structures selected from the group consisting of oxadiazole compounds of formulas (I) to (VI):

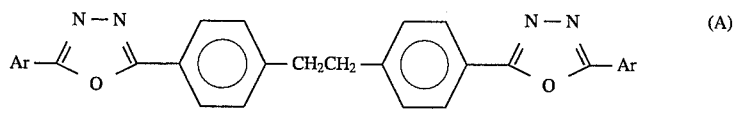

wherein Ar is phenyl group, or 4-tert-butylphenyl group.

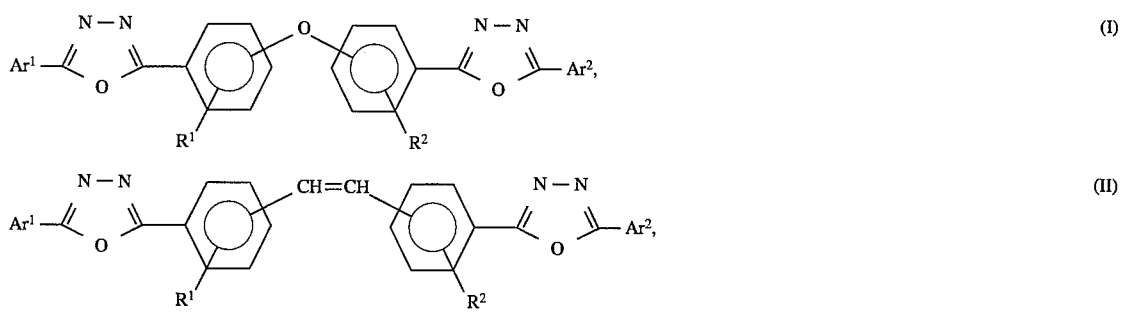

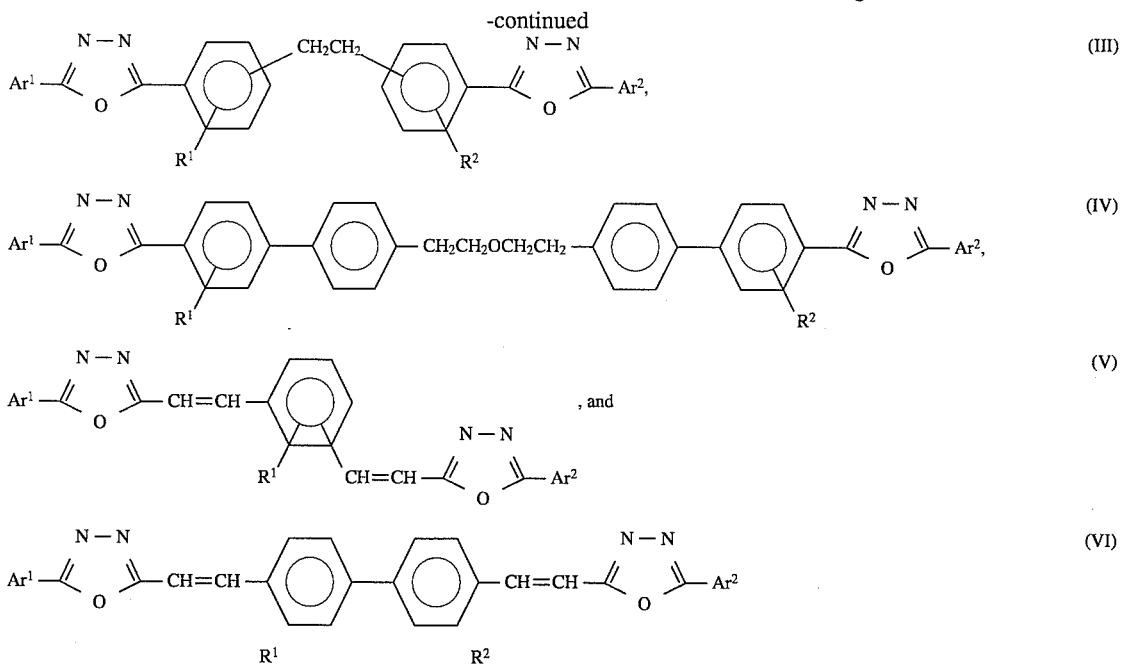

wherein $R^1$ and $R^2$ each represent hydrogen, a halogen, trifluoromethyl group, cyano group, nitro group, an alkyl group having 1 to 20 carbon atoms, an aryl group, an alkoxyl group having 1 to 20 carbon atoms, an aryloxy group, an alkylthio group, an amino group, an alkoxycarbonyl group, an acyl group, an sulfonyl group, a carbamoyl group, a sulfamoyl group, an alkylene dioxy group, or an alkylene dithio group; and $Ar^1$ and $Ar^2$ each represent an aromatic hydrocarbon ring, or an aromatic heterocyclic ring.

The first object of the present invention can also be attained by an electroluminescent device comprising a negative electrode, a positive electrode, and an organic compound layer which is interposed between the negative electrode and the positive electrode and comprises an oxadiazole compound having a plurality of aryl oxadiazole structures represented by formula (VII):

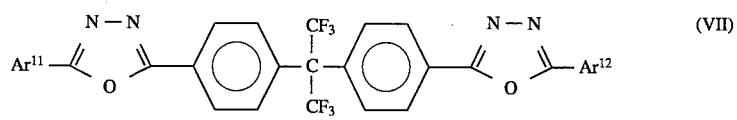

wherein $Ar^{11}$ and $Ar^{12}$ each represent an alkyl group having 1 to 20 carbon atoms, an aromatic hydrocarbon ring, or an aromatic heterocyclic ring.

The second object of the present invention can be attained by an oxadiazole compound represented by formula (VII):

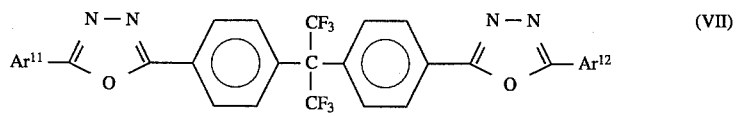

wherein $Ar^{11}$ and $Ar^{12}$ each represent an alkyl group having 1 to 20 carbon atoms, an aromatic hydrocarbon ring, or an aromatic heterocyclic ring.

The second object of the present invention can also be attained by a novel oxadiazole compound represented by formula (III-1):

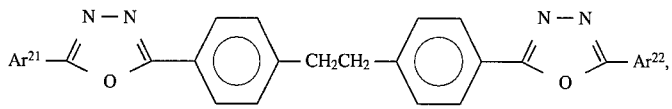

(III-1)

wherein Ar²¹ and Ar²² each represent an aryl group except phenyl group and 4-tert-butylphenyl group, or an aromatic heterocyclic ring.

The third object of the present invention can be attained by a method for producing an oxadiazole compound represented by formula (VII):

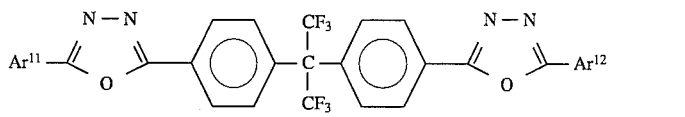

(VII)

by allowing a compound represented by formula (VIII) to react with a compound represented by formula (IX):

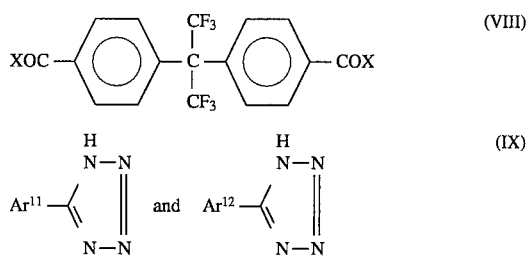

(VIII)

(IX)

wherein Ar¹¹ and Ar¹² each represent an alkyl group having 1 to 20 carbon atoms, an aromatic hydrocarbon ring or an aromatic heterocyclic ring; and X represents a halogen atom.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 14 is an infrared absorption spectrum (KBr tablet) of oxadiazole compound No. 32 shown in Table 1-(4).

DETAILED DESCRIPTION OF THE PREFERRED EMBODIMENT

Figure 1:
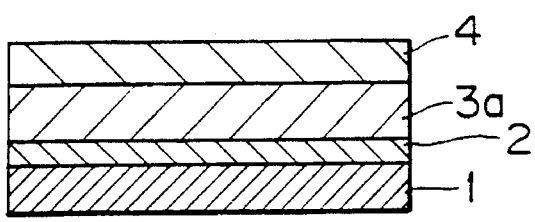
FIGS. 1 to 4 are schematic cross-sectional views of examples of an electroluminescent device of the present invention.

An example of an electroluminescent device according to the present invention comprises a negative electrode, a positive electrode, and an organic compound layer which is interposed between the negative electrode and the positive electrode and comprises at least one oxadiazole compound having a plurality of aryl oxadiazole structures selected from the group consisting of oxadiazole compounds of formulas (I) to (VI):

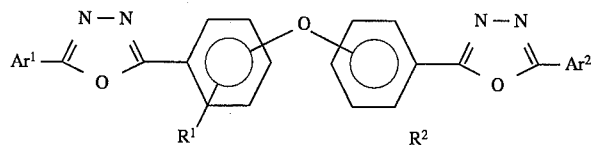

(I)

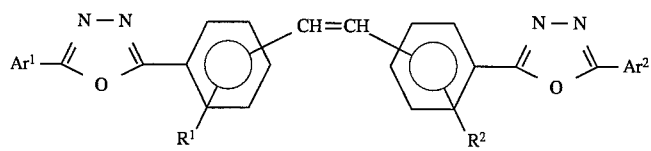

(II)

$$Ar^1 \underset{O}{\overset{N-N}{\diagdown}} \underset{R^1}{\text{—}\phantom{O}\text{—}} CH_2CH_2 \underset{R^2}{\text{—}\phantom{O}\text{—}} \underset{O}{\overset{N-N}{\diagdown}} Ar^2 \quad \text{(III)}$$

$$Ar^1 \underset{O}{\overset{N-N}{\diagdown}} \underset{R^1}{\text{—}\phantom{O}\text{—}\text{—}} CH_2CH_2OCH_2CH_2 \underset{R^2}{\text{—}\phantom{O}\text{—}\text{—}} \underset{O}{\overset{N-N}{\diagdown}} Ar^2 \quad \text{(VI)}$$

$$Ar^1 \underset{O}{\overset{N-N}{\diagdown}} -CH=CH-\underset{R^1\ CH=CH-\underset{O}{\overset{N-N}{\diagdown}}Ar^2}{\text{—}} , \text{ and} \quad \text{(V)}$$

$$Ar^1 \underset{O}{\overset{N-N}{\diagdown}} -CH=CH-\underset{R^1}{\text{—}\phantom{O}\text{—}}-CH=CH-\underset{O}{\overset{N-N}{\diagdown}}Ar^2 \quad \text{(VI)}$$

wherein $R^1$ and $R^2$ each represent hydrogen, a halogen, trifluoromethyl group, cyano group, nitro group, an alkyl group having 1 to 20 carbon atoms, an aryl group, an alkoxyl group having 1 to 20 carbon atoms, an aryloxy group, an alkylthio group, an amino group, an alkoxycarbonyl group, an acyl group, an sulfonyl group, a carbamoyl group, a sulfamoyl group, an alkylene dioxy group, or an alkylene dithio group; and $Ar^1$ and $Ar^2$ each represent an aromatic hydrocarbon ring, or an aromatic heterocyclic ring.

The alkyl group represented by $R^1$ or $R^2$ may have a substituent selected from the group consisting of hydroxyl group, cyano group, an alkyl group having 1 to 12 carbon atoms, phenyl group, a halogen atom, and a phenyl group having as a substituent an alkyl group or alkoxyl group having 1 to 12 carbon atoms.

Examples of the aryl group represented by $R^1$ or $R^2$ are an aromatic hydrocarbon ring, and an aromatic heterocyclic ring.

Examples of the aromatic hydrocarbon ring represented by $Ar^1$ and $Ar^2$ are styryl group, phenyl group, biphenyl group, terphenyl group, naphthyl group, anthryl group, acenaphthenyl group, fluorenyl group, phenanthryl group, indenyl group, and pyrenyl group, which may have a substituent selected from the group consisting or a halogen atom, hydroxyl group, cyano group, nitro group, an alkyl group, an alkoxyl group, an amino group, trifluoromethyl group, phenyl group, tolyl group, naphthyl group, and an aralkyl group.

Examples of the aromatic heterocyclic ring represented by $Ar^1$ and $Ar^2$ are pyridyl group, pyrimidyl group, furanyl group, pyronyl group, thiophenyl group, quinolyl group, benzofuranyl group, benzothiophenyl group, indolyl group, carbazolyl group, benzoxazolyl group, quinoxalyl group, benzimidazolyl group, pyrazolyl group, dibenzofuranyl group, dibenzothiophenyl group, pyrazinyl group, triazinyl group, pyrrolyl group, coumarinyl group, imidazolyl group, oxazolyl group, isooxazolyl group, thiazolyl group, indazolyl group, benzothiazolyl group, pyridazinyl group, cinnolyl group, and a quinazolyl group, which may have a substituent selected from the group consisting of a halogen atom, hydroxyl group, cyano group, nitro group, an alkyl group, an alkoxyl group, an amino group, trifluoromethyl group, phenyl group, tolyl group, naphthyl group, and an aralkyl group.

Examples of the aryloxy group represented by $R^1$ or $R^2$ are phenyl group and naphthyl group, which may have a substituent selected from the group consisting of an alkoxyl group having 1 to 12 carbon atoms, an alkyl group having 1 to 12 carbon atoms, and a halogen atom.

The alkylthio group represented by $R^1$ or $R^2$ is represented by formula (1):

$$-SR^3 \quad (1)$$

wherein $R^3$ is an alkyl group having 1 to 20 carbon atoms.

The amino group represented by $R^1$ or $R^2$ is represented by formula (2):

$$-N\begin{matrix}R^4\\R^5\end{matrix} \quad (2)$$

wherein $R^4$ and $R^5$ each represent hydrogen, an alkyl group having 1 to 20 carbon atoms, an acyl group such as acetyl group or benzoyl group, or an aryl group such as phenyl group, biphenyl group or naphthyl group. $R^4$ and $R^5$ in formula (2) may form a ring in combination with the nitrogen atom to which $R^4$ and $R^5$ are bonded, such as piperidyl group, or morpholyl group. $R^4$ and $R^5$ in formula (2) may form a ring in combination with a carbon atom in the aryl group to which the $R^4$ and $R^5$ bonded nitrogen atom in formula (2) is bonded, such as julolidyl group.

The alkoxycarbonyl group represented by $R^1$ or $R^2$ is represented by formula (3):

$$-COOR^6 \quad (3)$$

wherein $R^6$ represents an alkyl group having 1 to 20 carbon atoms, or an aryl group selected from the group consisting of the aromatic hydrocarbon ring and the aromatic heterocyclic ring, which are previously defined by $R^1$ or $R^2$.

The acyl group represented by $R^1$ and $R^2$ is represented by formula (4):

$$—COR^6 \quad (4)$$

wherein $R^6$ represents an alkyl group having 1 to 20 carbon atoms, or an aryl group selected from the group consisting of the aromatic hydrocarbon ring and the aromatic heterocyclic ring, which are previously defined by $R^1$ or $R^2$.

The sulfonyl group represented by $R^1$ or $R^2$ is represented by formula (5):

$$—SO_2R^6 \quad (5)$$

wherein $R^6$ represents an alkyl group having 1 to 20 carbon atoms, or an aryl group selected from the group consisting of the aromatic hydrocarbon ring and the aromatic heterocyclic ring, which are previously defined by $R^1$ or $R^2$.

The carbamoyl group represented by $R^1$ and $R^2$ is represented by formula (6):

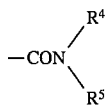

(6)

wherein $R^4$ and $R^5$ each represent hydrogen, an alkyl group having 1 to 20 carbon atoms, an acyl group, or an aryl group which are defined previously in formula (2). $R^4$ and $R^5$ in formula (6) may form a ring in combination with the nitrogen atom to which $R^4$ and $R^5$ are bonded.

The sulfamoyl group represented by $R^1$ and $R^2$ is represented by formula (7):

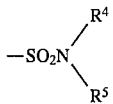

(7)

wherein $R^4$ and $R^5$ each represent hydrogen, an alkyl group having 1 to 20 carbon atoms, an acyl group, or an aryl group, which are defined previously in formula (2). $R^4$ and $R^5$ in formula (7) may from a ring in combination with the nitrogen atom to which $R^4$ and $R^5$ are bonded.

An example of the alkylene dioxy group represented by $R^1$ and $R^2$ is methylene dioxy group, and an example of the alkylene dithio group represented by $R^1$ and $R^2$ is methylene dithio group.

Another example of an electroluminescent device according to the present invention comprises a negative electrode, a positive electrode, and an organic compound layer which is interposed between the negative electrode and the positive electrode and comprises an oxadiazole compound having a plurality of aryl oxadiazole structure represented by formula (VII):

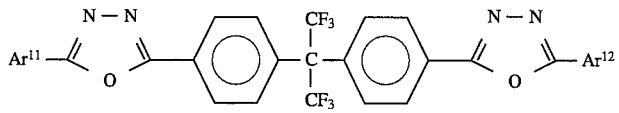

(VII)

wherein $Ar^{11}$ and $Ar^{12}$ each represent an alkyl group having 1 to 20 carbon atoms, or an aromatic hydrocarbon ring or aromatic heterocyclic ring.

Examples of the aromatic hydrocarbon ring represented by $Ar^{11}$ or $Ar^{12}$ are styryl group, phenyl group, biphenyl group, terphenyl group, naphthyl group, anthryl group, acenaphthenyl group, fluorenyl group, phenanthryl group, indenyl group, and pyrenyl group.

Examples of the aromatic heterocyclic ring represented by $Ar^{11}$ or $Ar^{12}$ are pyridyl group, pyrimidyl group, furanyl group, pyronyl group, thiophenyl group, quinolyl group, benzofuranyl group, benzothiophenyl group, indolyl group, carbazolyl group, benzoxazolyl group, quinoxalyl group, benzimidazolyl group, pyrazolyl group, dibenzofuranyl group, dibenzothiophenyl group, pyrazinyl group, triazinyl group, pyrrolyl group, coumarinyl group, imidazolyl group, oxazolyl group, isooxazolyl group, thiazolyl group, indazolyl group, benzothiazolyl group, pyridazinyl group, cinnolyl group, and quinazolyl group.

The alkyl group, the aromatic hydrocarbon ring or the aromatic heterocyclic ring represented by $Ar^{11}$ or $Ar^{12}$ may have any of the following substituents:

(1) a halogen atom, trifluoromethyl group, cyano group, and nitro group.

(2) a straight-chain or branched chain alkyl group having 1 to 6 carbon atoms, more preferably 1 to 4 carbon atoms.

(3) an aryl group which is selected from the group consisting of an aromatic hydrocarbon ring such as phenyl group, naphthyl group, anthryl group, acenaphthenyl group, fluorenyl group, phenanthryl group, indenyl group, or pyrenyl group; and an aromatic heterocyclic ring such as pyridyl group, pyrimidyl group, furanyl group, pyronyl group, thiophenyl group, quinolyl group, benzofuranyl group, benzothiophenyl, indolyl group, carbazolyl group, benzoxazolyl group, quinoxalyl group, benzoimidazolyl group, pyrazolyl group, dibenzofuranyl, and dibenzothiophenyl group, which aryl group may have a substituent such as a halogen atom, hydroxyl group, cyano group, nitro group, an alkyl group, an alkoxy group, and an amino group.

(4) an alkoxyl group having 1 to 6 carbon atoms.

(5) an aryloxy group including such an aryl group as defined in the above (3).

(6) an alkylthio group represented by formula (1)

$$—SR^7 \quad (1)$$

wherein $R^7$ is an alkyl group having 1 to 6 carbon atoms.

(7) an amino group represented by formula (2):

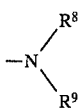

(2)

wherein $R^8$ and $R^9$ each represent hydrogen, an alkyl group having 1 to 6 carbon atoms, an acyl group such as acetyl group or benzoyl group, or an aryl group as defined in the above (3), and $R^8$ and $R^9$ may form a ring in combination with the nitrogen atom, such as a piperidyl group, or morpholyl group, or may form a ring in combination with a carbon atom in the aryl group to which the $R^8$ and $R^9$ bonded nitrogen atom is bonded, such as julolidyl group.

(8) an alkoxycarbonyl group represented by —COOR$^{10}$ wherein $R^{10}$ represents the same alkyl group as defined in (2) or the same aryl group as defined in (3).

(9) an acyl group represented by —COR¹⁰, an sulfonyl group represented by —SO₂R¹⁰, a carbamoyl group represented by

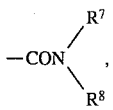

or a sulfamonyl group represented by

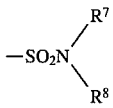

wherein $R^7$, $R^8$ and $R^{10}$ are respectively the same as those defined in the above; $R^7$ and $R^8$ may form a ring in combination with the carbon atom in the adjacent aryl group.

(10) an alkylene dioxy group such as methylene dioxy group, and an alkylene dithio group such as methylene dithio group.

(11) a styryl group represented by —CH=CH—C₆H₄—R¹¹ wherein $R^{11}$ represents the same substituent as that defined in (1) to (10).

As mentioned previously, the oxadiazole compound of formula (VII) is a novel oxadiazole compound.

Furthermore, the oxadiazole compound of formula (III-1) is also a novel oxadiazole compound:

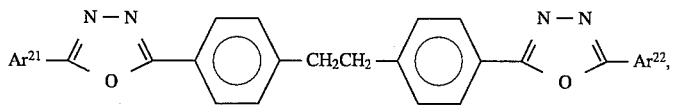

wherein $Ar^{21}$ and $Ar^{22}$ each represent an aryl group except phenyl group and 4-tert-butylphenyl group, or an aromatic heterocyclic ring.

In the oxadiazole compound of formula (III-1), examples of the aryl group represented by $Ar^{21}$ and $Ar^{22}$ are a substituted phenyl group excluding 4-butylphenyl group, naphthyl group, anthryl group, and phenanthryl group. An example of the aromatic heterocyclic ring represented by $Ar^{21}$ and $Ar^{22}$ is pyridyl ring.

Examples of a substituent of the aryl group represented by $Ar^{21}$ and $Ar^{22}$ are a straight-chain or branched chain alkyl group having 1 to 6 carbon atoms, more preferably having 1 to 4 carbon atoms; an alkoxyl group including the above-mentioned alkyl group; a halogen atom such as chlorine or bromine; trifluoromethyl group; cyano group; nitro group; and an alkoxyl group including as a substituent, for example, an aryl group such as phenyl group, naphthyl group or anthryl group, the above-mentioned alkyl group or aryl group.

In the electroluminescent device according to the present invention, the organic compound layer may comprise (1) an electroluminescent layer comprising any of the above-mentioned oxadiazole compounds, and a hole-transporting layer, (2) an electron-transporting layer comprising any of the above-mentioned oxadiazole compounds, and a hole-transporting luminescent layer, (3) an electroluminescent layer and an electron-transporting layer, one of the electroluminescent layer or the electron-transporting layer comprising any of the above-mentioned oxadiazole compounds, or (4) an electro-luminescent layer, an electron-transporting layer, and a hole-transporting layer, the electroluminescent layer being interposed between the electron-transporting layer and the hole-transporting layer, and the electron-transporting layer comprising any of the above-mentioned oxadiazole compounds.

The oxadiazole compounds for use in the present invention are particularly useful as luminescent materials and electron-transporting materials for use in the electroluminescent device and have much better film-forming properties in comparison with conventional materials. Furthermore, when the oxadiazole compounds for use in the present invention are employed as a component for an electroluminescent material, it is possible to fabricate an electroluminescent device with a minimum deterioration with time.

The oxadiazole compounds are particularly useful as a component in an electron-transporting layer for an electroluminescent device which emits blue light.

An electroluminescent device containing an electron-transporting compound with excellent film-forming properties stable with time, and capable of emitting light with high luminance, can be fabricated when the oxadiazole compounds for use in the present invention are employed as a component in an organic electron-transporting layer for (i) an electroluminescent device which comprises a positive electrode, a negative electrode, and an organic compound layer comprising an organic hole-transporting luminescent layer and an organic electron-transporting layer, which are successively formed on the positive electrode and interposed located between the positive electrode and the negative electrode, or for (ii) an electroluminescent device which comprises a positive electrode, a negative electrode, and an organic compound layer comprising an organic hole-transporting layer, an organic electro-luminescent layer and an organic electron-transporting layer which are successively overlaid on the positive electrode, and interposed between the positive electrode and the negative electrode.

The oxadiazole compounds for use in the present invention can also be used as fluorescent pigments, more specifically fluorescent brightening agents and laser pigments, and also as charge transporting materials for an organic photoconductor.

The oxadiazole compounds for use in the present invention can be formed into a film layer by a film formation method such as vacuum deposition and solvent coating, so that an organic film layer comprising the oxadiazole compound is made and interposed between a negative electrode and a positive electrode, whereby an electroluminescent device according to the present invention is fabricated. It is also possible to add one or more additives to the film layer comprising the oxadiazole compound when the electroluminescent device is fabricated. Moreover, a charge-injection transporting layer can be provided between the organic compound layer and one of the electrodes for improving the charge-injection efficiency from the electrode.

As a material for the positive electrode, metals, alloys, and compounds having a large work function, such as nickel, gold, platinum, palladium, their alloys, tin oxide, ITO (indium-tin-oxide) and copper iodide, and their alloys; and electroconductive polymers such as poly (3-methylthiophene) and polypyrrole.

As a material for the negative electrode, materials with a small work function such as silver, tin, copper, magnesium, manganese, aluminum, and their alloys can be employed. It is desirable that at least one of the material for the positive electrode or the material for the negative electrode be transparent in the region of the wavelength of the light emitted by the electro-luminescent device. More specifically, it is desirable that the material for at least one electrode have an optical transmission of 80% or more.

FIGS. 1 to 4 are schematic illustrations of the structures of representative examples of an electro-luminescent devices according to the present invention.

In FIGS. 1 to 4, reference numeral 1 represents a substrate; reference numerals 2, 4, electrodes; 3a, an electroluminescent layer; reference numeral 3a, an electron-transporting layer; and reference numeral 3c, a hole-transporting layer.

An electroluminescent device shown in FIG. 1 comprises a substrate 1, and an electrode 2, an electro-luminescent layer 3a and an electrode 4, which are successively overlaid on the substrate 1.

Figure 2:
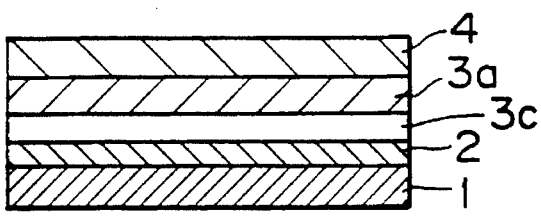

FIG. 2 shows an electroluminescent device comprising a hole-transporting layer 3c which is interposed between the electrode 2 and the electro-luminescent layer 3a in the same electroluminescent device as shown in FIG. 1.

Figure 3:
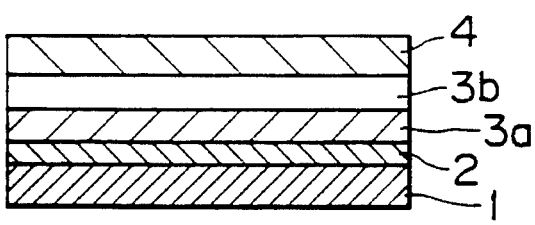

FIG. 3 shows an electroluminescent device comprising an electron-transporting layer 3b which is interposed between the electroluminescent layer 3a and the electrode 4 in the same electroluminescent device as shown in FIG. 1.

Figure 4:
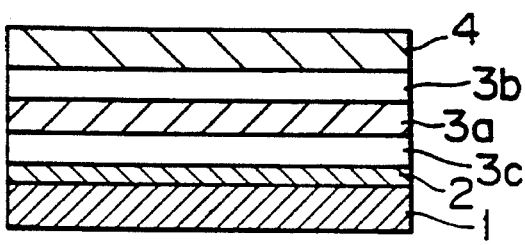

FIG. 4 shows an electroluminescent device comprising a support 1, and an electrode 2, a hole-transporting layer 3c, an electroluminescent layer 3a, an electron-transporting layer 3b and an electrode 4 which are successively overlaid on the substrate 1.

The electroluminescent device according to the present invention comprises the above-mentioned layers successively overlaid on a transparent substrate such as glass plate. Furthermore, the electroluminescent device may comprise a protective layer, or may be incorporated in a cell sealed with a silicone oil, in order to improve the stability of the electroluminescent device and to protect the same from the water contained in air.

Specific examples of the oxadiazole compound represented by any of formulas (I) to (VII) and (III-I) are shown in Table 1. The oxadiazole compounds for use in the present invention are not limited to these examples.

TABLE 1-(1)

| Compound No. | Ar¹ | Ar² | R¹ | R² |
|---|---|---|---|---|
| 1 | phenyl | phenyl | H | H |
| 2 | Et₂N-phenyl | Et₂N-phenyl | H | H |
| 3 | naphthyl | naphthyl | H | H |
| 4 | N-phenyl | N-phenyl | H | H |
| 5 | anthryl | anthryl | H | H |

TABLE 1-(1)-continued
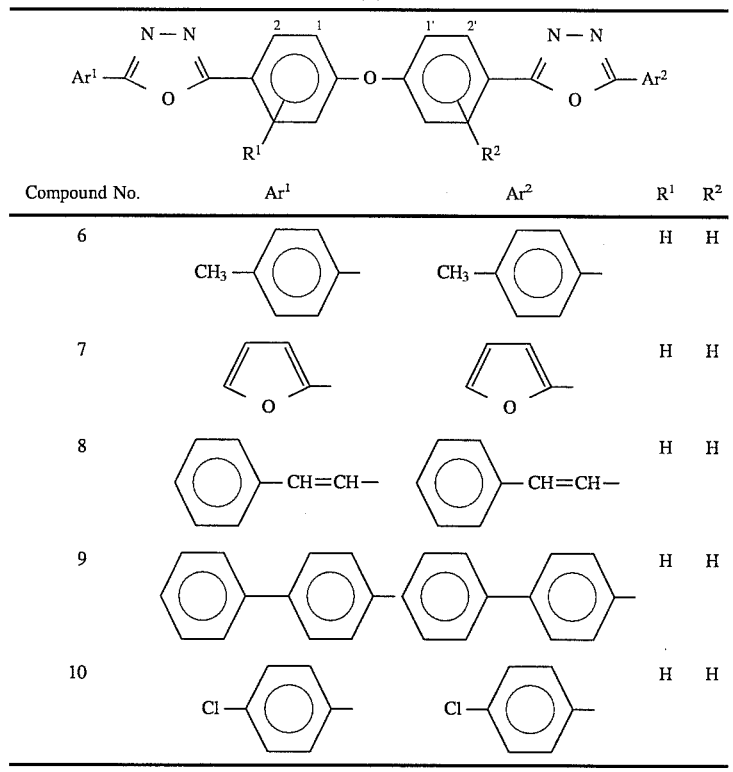
TABLE 1-(2)
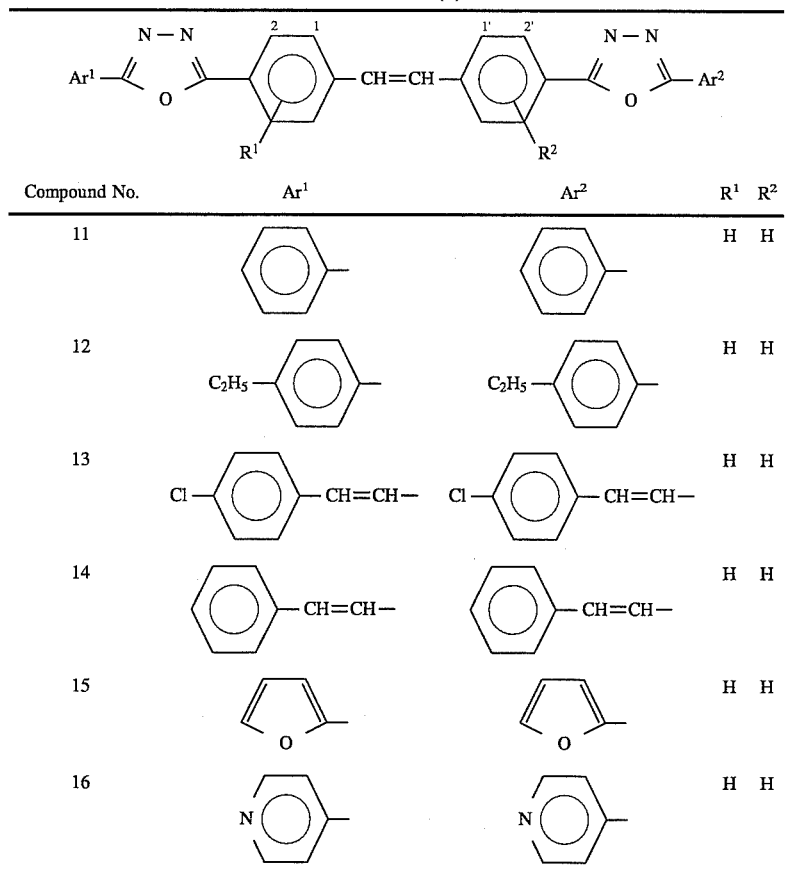

TABLE 1-(2)-continued

Structure:
Ar¹-C(=N-N-O)-[benzene(2,1; R¹)]-CH=CH-[benzene(1',2'; R²)]-C(=N-N-O)-Ar²

| Compound No. | Ar¹ | Ar² | R¹ | R² |
|---|---|---|---|---|
| 17 | 4-CF₃-C₆H₄- | 4-CF₃-C₆H₄- | H | H |
| 18 | 1-naphthyl | 1-naphthyl | H | H |

TABLE 1-(3)

Structure:
Ar¹-C(=N-N-O)-[benzene(2,1; R¹)]-CH₂CH₂-[benzene(1',2'; R²)]-C(=N-N-O)-Ar²

| Compound No. | Ar¹ | Ar² | R¹ | R² |
|---|---|---|---|---|
| 19 | 4-CN-C₆H₄- | 4-CN-C₆H₄- | H | H |
| 20 | C₆H₅- | C₆H₅- | H | H |
| 21 | 4-CH₃-C₆H₄- | 4-CH₃-C₆H₄- | H | H |
| 22 | C₆H₅-CH=CH- | C₆H₅-CH=CH- | H | H |
| 23 | 1-naphthyl | 1-naphthyl | H | H |
| 24 | 4-pyridyl | 4-pyridyl | H | H |
| 25 | 4-(C₆H₅-C₆H₄-C₆H₄-)-C₆H₄- | | H | H |

TABLE 1-(3)-continued
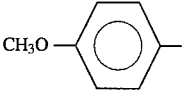
| Compound No. | Ar¹ | Ar² | R¹ | R² |
|---|---|---|---|---|
| 26 | CH₃O—⟨phenyl⟩— | CH₃O—⟨phenyl⟩— | H | H |
| 27 | Cl—⟨phenyl⟩— | Cl—⟨phenyl⟩— | H | H |
TABLE 1-(4)
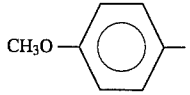
| Compound No. | Ar²¹, Ar²² | Compound No. | Ar²¹, Ar²² |
|---|---|---|---|
| 28 | ⟨biphenyl⟩— | 36 | CH₃OCO—⟨phenyl⟩— |
| 29 | CH₃O—⟨phenyl⟩— | 37 | ⟨naphthyl⟩— |
| 30 | Cl—⟨phenyl⟩— | 38 | NO₂—⟨phenyl⟩— |
| 31 | CH₃—⟨phenyl⟩— | 39 | ⟨phenyl⟩—OCH₂— |
| 32 | ⟨naphthyl⟩— | | |
| 33 | CN—⟨phenyl⟩— | | |
| 34 | ⟨pyridyl⟩— | | |

TABLE 1-(4)-continued $$Ar^{21} \underset{O}{\overset{N-N}{\diagup\!\!\!\diagdown}} \text{—}\phantom{}\!\!\!\bigcirc\!\!\!\phantom{}\text{—}CH_2CH_2\text{—}\phantom{}\!\!\!\bigcirc\!\!\!\phantom{}\text{—}\underset{O}{\overset{N-N}{\diagdown\!\!\!\diagup}} Ar^{22}$$

| Compound No. | Ar²¹, Ar²² | Compound No. | Ar²¹, Ar²² |
|---|---|---|---|
| 35 | anthracenyl | | |

TABLE 1-(5)

| Compound No. | Ar¹ | Ar² | R¹ | R² |
|---|---|---|---|---|
| 40 | phenyl | phenyl | H | H |
| 41 | NC–C₆H₄– | NC–C₆H₄– | H | H |
| 42 | naphthyl | naphthyl | H | H |
| 43 | pyridyl | pyridyl | H | H |
| 44 | (CH₃)₃C–C₆H₄– | (CH₃)₃C–C₆H₄– | H | H |
| 45 | C₆H₅–CH=CH– | C₆H₅–CH=CH– | H | H |
| 46 | CH₃–C₆H₄– | CH₃–C₆H₄– | H | H |

TABLE 1-(6)
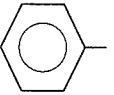
| Compound No. | Ar¹ | Ar² | R¹ |
|---|---|---|---|
| 47 | 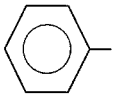 | 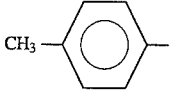 | H |
| 48 | 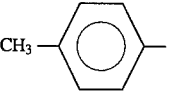 | 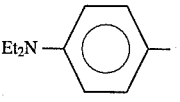 | H |
| 49 | 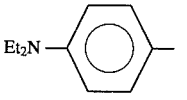 | 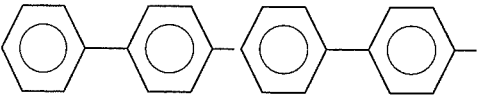 | H |
| 50 | 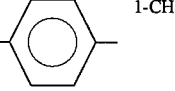 | 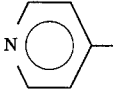 | 1-CH₃ |
| 51 | 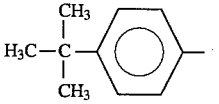 | 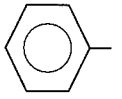 | H |
TABLE 1-(7)
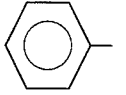
| Compound No. | Ar¹ | Ar² | R¹ |
|---|---|---|---|
| 52 | 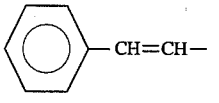 | 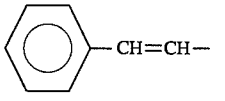 | H |
| 53 | 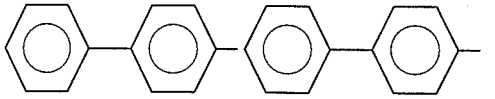 | 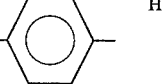 | H |
| 54 | 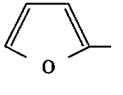 | 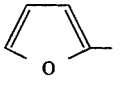 | H |
| 55 | 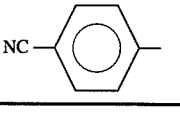 |  | H |
| 56 | NC—⬡— | NC—⬡— | H |

TABLE 1-(8)

Ar¹—[oxadiazole]—CH=CH—[phenyl(R¹)]—[phenyl(R²)]—CH=CH—[oxadiazole]—Ar²

| Compound No. | Ar¹ | Ar² | R¹ | R² |
|---|---|---|---|---|
| 57 | phenyl- | phenyl- | H | H |
| 58 | 4-CH₃-phenyl- | 4-CH₃-phenyl- | H | H |
| 59 | 4-Cl-phenyl- | 4-Cl-phenyl- | H | H |
| 60 | 3-NC-phenyl- | 3-NC-phenyl- | H | H |
| 61 | 4-pyridyl- | 4-pyridyl- | H | H |

TABLE 1-(9)

Ar¹—[oxadiazole]—CH=CH—[phenyl 3,2 (R¹)]—[phenyl 2',3' (R²)]—CH=CH—[oxadiazole]—Ar²

| Compound No. | Ar¹ | Ar² | R¹ | R² |
|---|---|---|---|---|
| 62 | phenyl- | phenyl- | 2-CH₃ | 2'-CH₃ |
| 63 | 4-tert-butyl-phenyl- | 4-tert-butyl-phenyl- | 2-CH₃ | 2'-CH₃ |
| 64 | 4-CF₃-phenyl- | 4-CF₃-phenyl- | 2-COOCH₃ | 2-COOCH₃ |
| 65 | 1-naphthyl- | 1-naphthyl- | 3-Cl | 3-Cl |

TABLE 1-(9)-continued
| Compound No. | Ar¹ | Ar² | R¹ | R² |
|---|---|---|---|---|
| 66 | phenyl | phenyl | 3-Cl | 3-Cl |
TABLE 1-(10)
| Compound No. | Ar¹¹, Ar¹² |
|---|---|
| 67 | 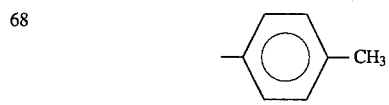 |
| 68 | 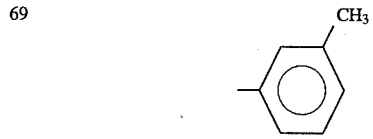 |
| 69 |  |
| 70 |  |
| 71 |  |
| 72 |  |
| 73 |  |
TABLE 1-(10)-continued
| Compound No. | Ar¹¹, Ar¹² |
|---|---|
| 74 |  |
| 75 |  |
| 76 |  |
| 77 | 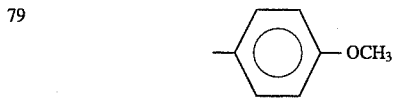 |
| 78 | 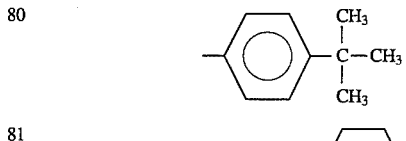 |
| 79 | 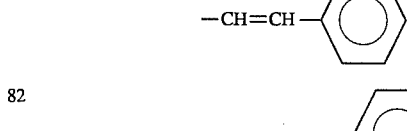 |
| 80 | 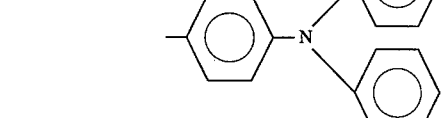 |
| 81 | —CH=CH— phenyl |
| 82 | triphenylamine group |

TABLE 1-(10)-continued

Structure (Compounds 83-93):
Ar¹¹—(N=N/oxadiazole)—C₆H₄—C(CF₃)(CF₃)—C₆H₄—(oxadiazole/N=N)—Ar¹²

| Compound No. | Ar¹¹, Ar¹² |
|---|---|
| 83 | —CH₂—C₆H₅ (benzyl) |
| 84 | pyridyl |
| 85 | thienyl (S) |
| 86 | 9-ethylcarbazol-3-yl (N—C₂H₅) |
| 87 | —C₆H₄—CH=CH—C₆H₅ |
| 88 | —C₆H₄—CH=CH—C₆H₄—C₂H₅ |
| 89 | naphthyl |
| 90 | anthryl |
| 91 | naphthyl |
| 92 | biphenyl (methyl-substituted) |
| 93 | —C₆H₄—OCH₃ |

TABLE 1-(10)-continued

Structure (Compounds 94-99): same as above

| Compound No. | Ar¹¹, Ar¹² |
|---|---|
| 94 | —C₆H₄—C₆H₄—CH₂CH₃ (biphenyl-ethyl) |
| 95 | —C₆H₄—C₆H₄—CH₂CH₂CH₃ |
| 96 | —C₆H₄—CF₃ |
| 97 | methyl-naphthyl with OCH₂CH₃ |
| 98 | —C₆H₄—CH=CH—C₆H₅ |
| 99 | 9-ethylcarbazolyl (N—C₂H₅) |

Of the oxadiazole compounds represented by formula (I) to (VII) for use in the present invention, the oxadiazole compound represented by (VII) is preferably employed in the present invention because the deterioration of the luminance with time is minimal.

The oxadiazole compound of formula (VII) can be prepared in accordance with the following reaction scheme including Step A-1 and Step B:

Step A-1

2,2-bis(4-carbazoylphenyl) hexafluoro propane represented by formula (VII-1) is allowed to react with a compound represented by formula (VII-2) to produce a compound represented by formula (VIII-3):

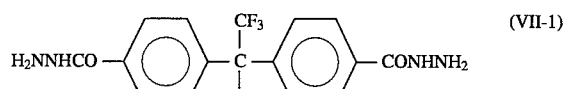
(VII-1)

$$Ar^{11}COX \quad \text{and} \quad Ar^{12}COX \quad \text{(VII-2)}$$

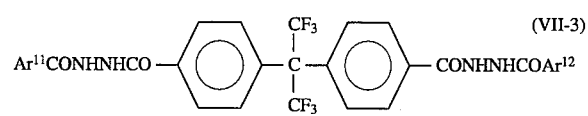
(VII-3)

wherein $Ar^{11}$ and $Ar^{12}$ are respectively the same as previously defined in formula (VII); and X represents a halogen atom.

Step B

The above obtained compound represented by formula (VII-3) is subjected to dehydration, so that the oxadiazole compound of formula (VII) according to the present invention is obtained.

The 2,2-bis(4-carbazoylphenyl) hexafluoro propane of formula (VII-1) serving as a starting material for the preparation of the oxadiazole compound of formula (VII) can be easily produced by allowing an ester derivative of formula (VII-6) to react with hydrazine.

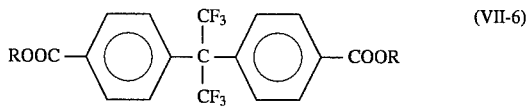

(VII-6)

wherein R represents an alkyl group.

Alternatively, the oxadiazole compound of formula (VII) can be produced in accordance with the following reaction scheme including Step A-2 and Step B:

Step A-2

A compound of formula (VII-4) is allowed to react with a compound of formula (VII-5), so that a compound of formula (VII-3) is obtained.

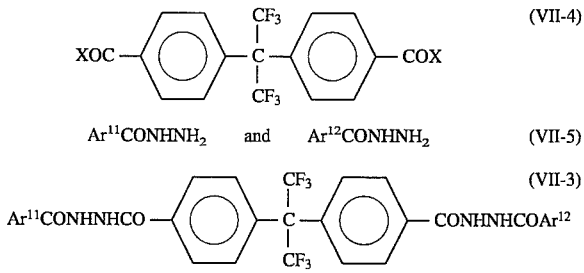

wherein $Ar^{11}$ and $Ar^{12}$ are respectively the same as previously defined; and X represents a halogen atom.

Step B

The above obtained compound of formula (VII-3) is subjected to dehydration, so that the oxadiazole compound of formula (VII) according to the present invention is obtained.

The compound of formula (VII-4) employed as a starting material for the preparation of the oxadiazole compound of formula (VII) can be easily produced by allowing a carboxylic acid corresponding to the compound of formula (VII-4) to react with a halogenation agent such as thienyl chloride.

The compound of the above-mentioned formula (VII-5) is conventionally known and can be easily obtained.

The previously mentioned Steps A-1 and A-2 are usually carried out in the presence of a basic catalyst.

Examples of the basic catalyst include organic basic catalysts such as pyrizine, pyrizine derivatives, triethylamine, tributylamine, triethanolamine, quinoline, piperazine, and morpholine; and inorganic basic catalysts such as sodium hydroxide, potassium hydroxide, and sodium carbonate. In the above reaction, the organic basic catalysts are preferably used.

As a reaction solvent, any materials which dissolve at least the compound of formula (VII-3) can be employed. In particular, it is preferable to use as the reaction solvent alcohol solvents such as ethanol and butanol; ether solvents such as dioxane and tetrahydrofuran; aromatic solvents such as benzene, toluene, chlorobenzene and nitrobenzene; N,N-dimethylformamide; and dimethyl sulfoxide.

When any of the above-mentioned organic basic catalysts such as pyridine is used in an excessive amount, it can be employed as a reaction solvent as well. The reaction is usually completed within several tens minutes to several hours at room temperatures to 150° C.

It is preferable that 2 to 3 moles of the compound of formula (VII-2) be employed to one mole of the compound of formula (VII-1) in the previously mentioned Step A-1, and that 2 to 3 moles of the compound of formula (VII-5) be employed to one mole of the compound of formula (VII-4) in Step A-2.

The oxadiazole derivative represented by formula (VII) of the present invention can be obtained by dehydrating the compound of formula (VII-3) to carry out ring closure by use of a dehydrating agent such as phosphorus oxychloride, thionyl chloride, polyphosphoric acid, boric acid, or toluenesulfonic acid in Step B. In Step B, the same reaction solvent as employed in Steps A-1 and A-2 can also be employed. It is preferable that aromatic solvents such as chlorobenzene, dichlorobenzene, xylene, and nitrobenzene; or halogen-based solvents such as trichloroethane and trichloroethylene be employed as the reaction solvent. It is suitable that the dehydrating agent be used in an amount of 0.1 to 10 moles to one mole of the compound of formula (VII-3). When the hydrating agent such as phosphorus oxychloride is employed in an excessive amount, it can be employed as a reaction solvent as well. The reaction is usually completed within several tens minutes to several tens hours at 50° C. to 300° C.

Alternatively, the oxadiazole derivative of formula (VII) according to the present invention can be prepared by allowing the compound of the previously mentioned formula (VII-4) to react with a tetrazole compound of formula (VII-7) as follows:

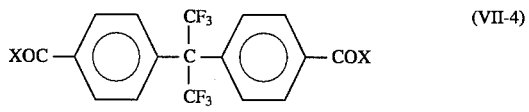

(VII-4)

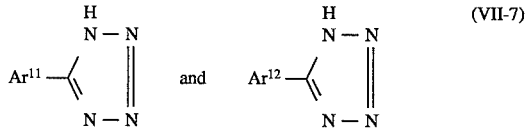

(VII-7)

wherein $Ar^{11}$ and $Ar^{12}$ each represent an alkyl group having 1 to 20 carbon atoms, an aromatic hydrocarbon ring or an aromatic heterocyclic ring.

The tetrazole compound represented by formula (VII-7) can be synthesized by a conventionally known method such as a method described in Synthesis 71 (1973).

Moreover, it is has been confirmed that the oxadiazole compound of formula (VII) can be easily synthesized by the reaction between the compound of formula (VI-4) and the tetrazole compound of formula (VII-7) in accordance with an oxadiazole synthesis by R. D. Huisgen et al. Furthermore, the methods described in Angew. Chem., 72, 366 (1960); Chem. Ber., 93, 2106 (1960); Tetrahedron, 11, 241 (1960); or Chem. Ber., 98, 2966 (1965) can also be applied to the preparation of the oxadiazole compound of formula (VII) of the present invention.

The oxadiazole compound of formula (III-1) of the present invention can be prepared in accordance with a reaction scheme shown in the following Table 2:

TABLE 2

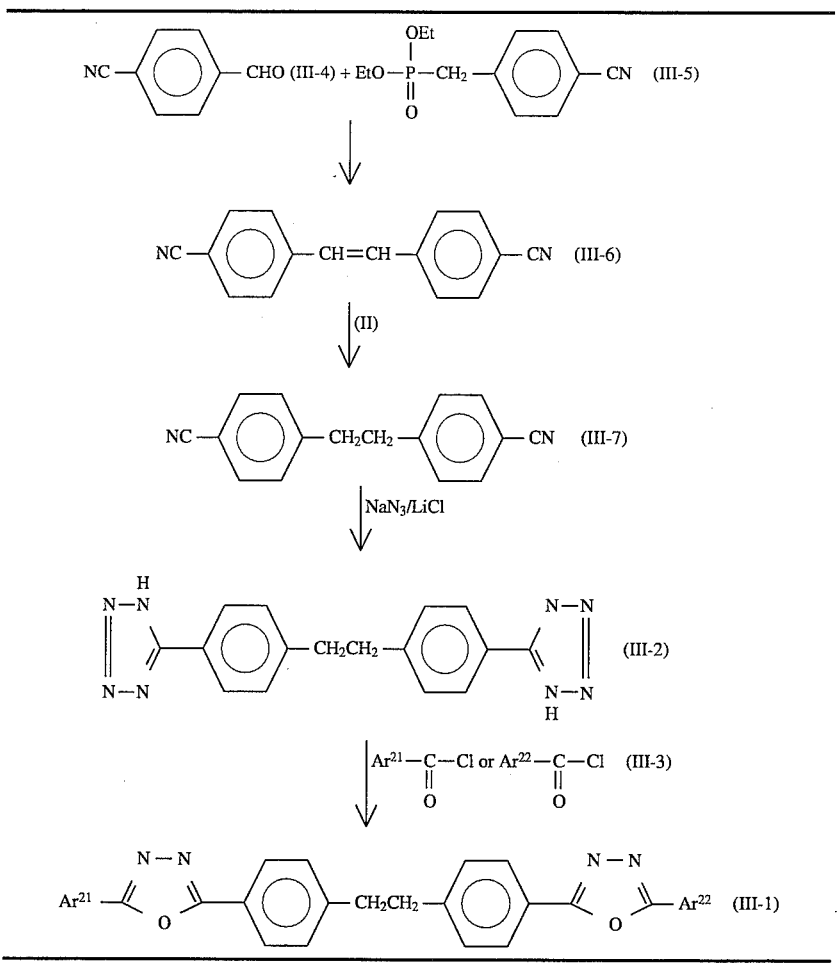

As is shown in the above Table 2, 4-cyanobenzaldehyde of formula (III-4) is allowed to react with 4-cyano dibenzyl diethylphosphonate of formula (III-5) to obtain 4,4'-dicyanostilbene of formula (III-6).

Subsequently, 4,4'-dicyanostilbene of formula (III-6) is subjected to hydrogenation, so that 4,4'-dicyanodibenzyl of formula (III-7) is obtained. The thus obtained 4,4'-dicyanodibenzyl of formula (III-7) is allowed to react with sodium azide in the presence of lithium chloride, whereby 5,5'-(4, 4'-dibenzyl) ditetrazole of formula (III-2) is obtained. The 5,5'-(4,4'-dibenzyl) ditetrazole represented by formula (III-2) is allowed to react with a carboxylic acid chloride represented by formula (III-3), so that the oxadiazole compound represented by formula (III-1) according to the present invention can be obtained.

The intermediates produced during the preparation of the oxadiazole compound of formula (III-1) in the above synthesis can be easily purified, so that the oxadiazole compound of formula (III-1), which is a final product, can also be easily obtained with high purity.

The oxadiazole compound of formula (III-1) according to the present invention can also be synthesized in accordance with the conventional method shown in the following Table 3:

TABLE 3

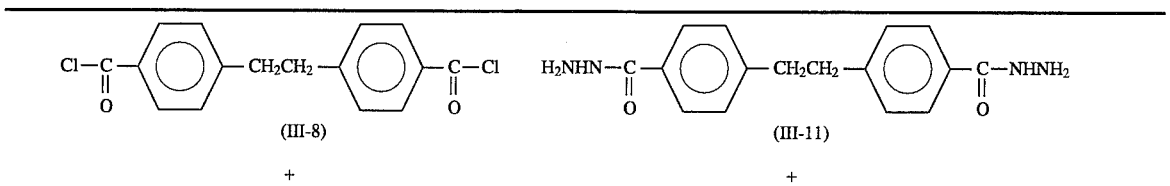

+                                       +

TABLE 3-continued

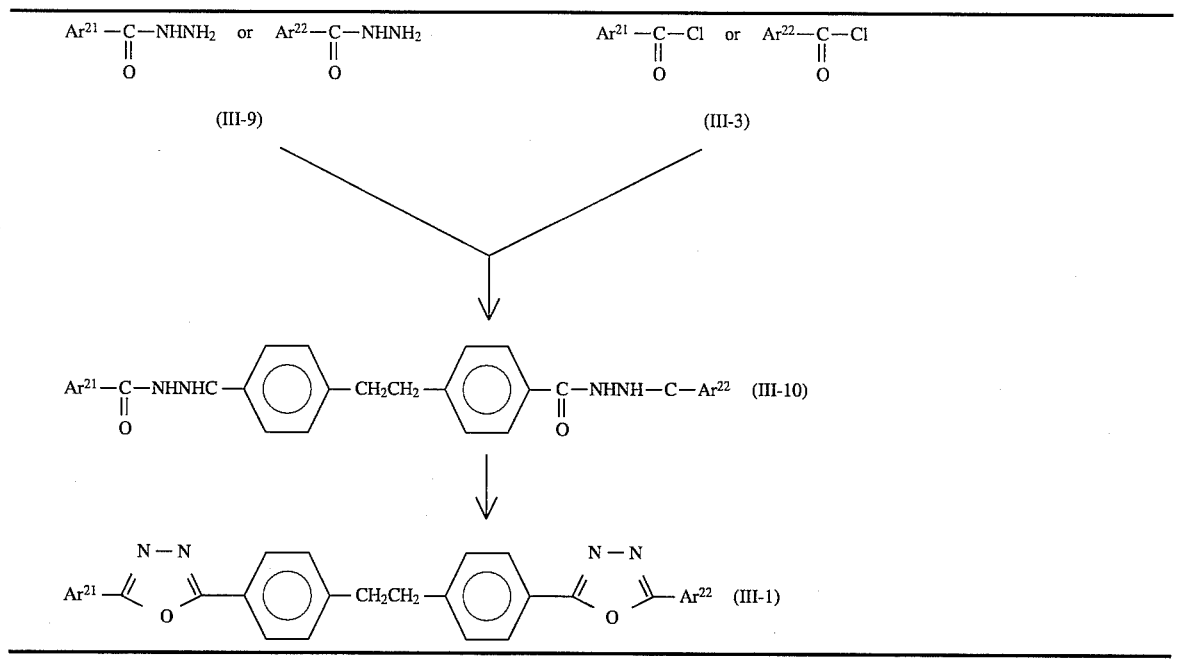

Dibenzyl-4,4'-dicarboxylic acid chloride of formula (III-8) is allowed to react with a carboxylic acid mono hydrazide of formula (III-9) to prepare an acyl hydrazine derivative of formula (III-10). The acyl hydrazine derivative of formula (III-10) is subjected to dehydration to form a ring by use of a hydrating agent such as phosphorus pentachloride, phosphonic acid or thionyl chloride, so that the oxadiazole compound represented by formula (III-1) according to the present invention can be obtained.

Alternatively, dibenzyl 4,4'-dicarboxylic acid dihydrazide of formula (III-11) is allowed to react with a carboxylic acid chloride of formula (III-3), whereby the acyl hydrazine derivative of formula (III-10) is obtained. Subsequently, the acyl hydrazine derivative represented by formula (III-10) is subjected to dehydration to form a ring in the same manner as mentioned above, so that the oxadiazole compound represented by formula (III-1) according to the present invention can be obtained.

The above method, however, has the shortcomings that the solubility of the acyl hydrazine derivative of formula (III-10) in a solvent, which is produced as an intermediate, is so poor that the purification thereof is difficult, and colored impurities are produced in a slight amount in the succeeding dehydration and ring formation step, so that it is difficult to obtain the oxadiazole compound of formula (III-1) with high purity.

When the oxadiazole compound of formula (III-1) of the present invention is employed as a constituent of an electron-transporting layer for the electroluminescent device with the structure as shown in FIG. 3 or FIG. 4, the materials employed for the electroluminescent layer and hole-transporting layer will now be explained.

As an organic compound employed for the hole-transporting layer, any organic compound which, in a solid state, emits a strong fluorescent light and has excellent hole-transporting capability can be employed.

Examples of such a compound include triphenylamines, stilbene derivatives, and pyrazoline derivatives. Specific examples of these compounds are shown in Table 4.

TABLE 4

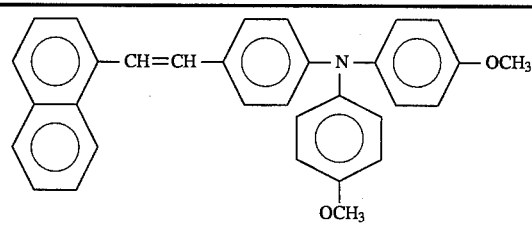
(1)

TABLE 4-continued
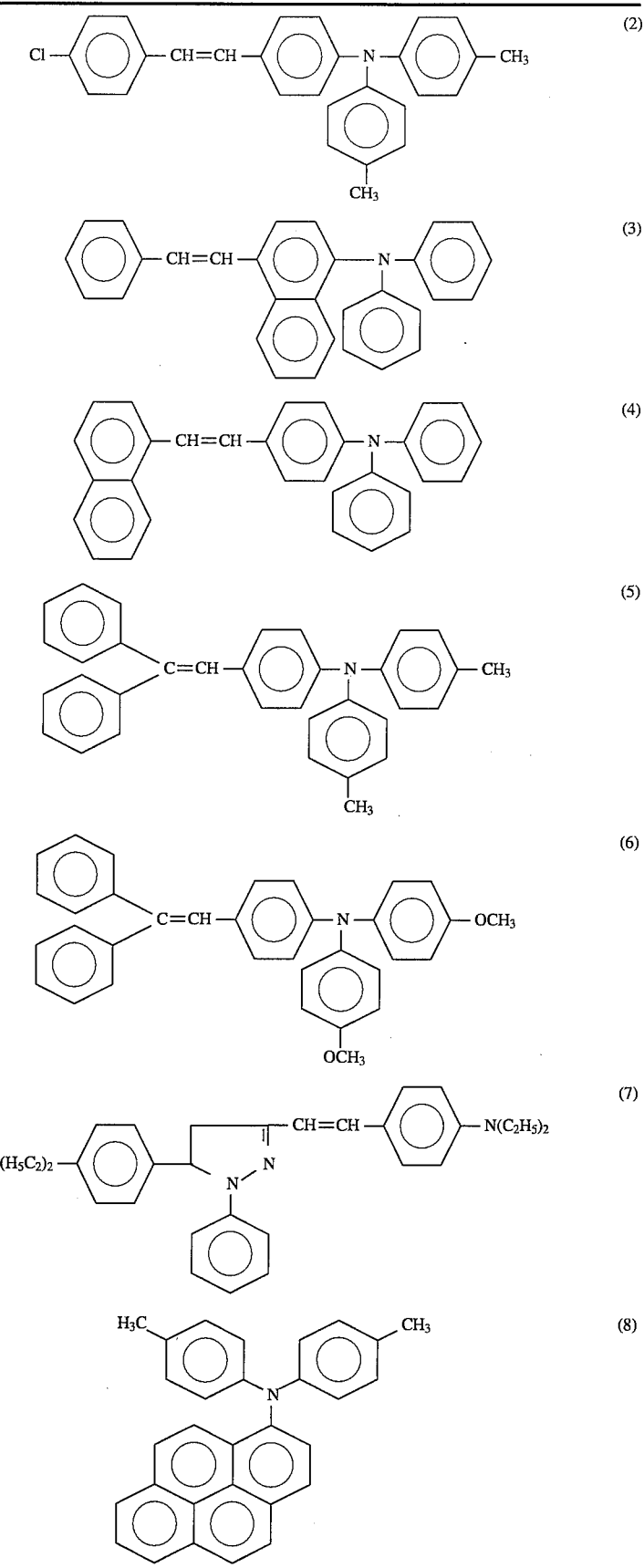

TABLE 4-continued

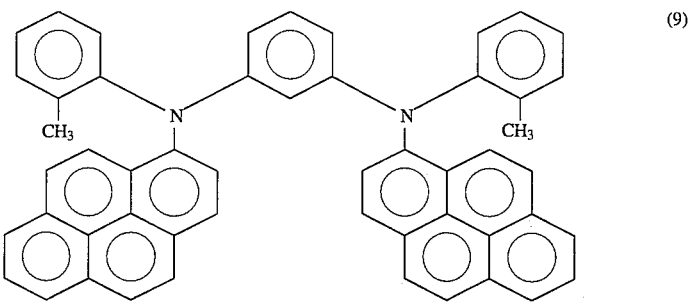
(9)

Among the compounds shown in Table 4, compounds (2), (3), (4), and (5) are preferably employed to emit blue light. These compounds can also be employed in an electroluminescent layer of the electroluminescent device shown in FIG. 4.

Conventionally known hole-transporting materials can be employed in the hole-transporting layer of each of the electroluminescent devices shown in FIGS. 2 and 4, Examples of the hole-transporting material are as follows: (1) triazole derivatives as disclosed in U.S. Pat. No. 3,112, 197; (2) oxadiazole derivatives as disclosed in U.S. Pat. No. 3,189,447; (3) imidiazole derivatives as disclosed in Japanese Patent Publication 37-16096; (4) polyarylalkane derivatives as disclosed in U.S. Pat. Nos. 3,615,402, 3,820, 989 and 3,542,544, Japanese Patent Publications 45-5558 and 51-10983, and Japanese Laid-Open Patent Applications 51-93224, 55-17105, 56-4148, 55-108667, 55-156953 and 56-36656; (5) pyrazoline derivatives and pyrazolone derivatives as disclosed in U.S. Pat. Nos. 3,180,729 and 4,278,746, Japanese Laid-Open Patent Application 55-880646, 55-88065, 49-105537, 55-51086, 56-80051, 56-88141, 57-45545, 54-112637 and 55-74546; (6) phenylenediamine derivatives as disclosed in U.S. Pat. No. 3,615,404, Japanese Patent Publication 51-10105, 46-3712 and 47-25336, and Japanese Laid-Open Patent Applications 54-53435, 54-110536 and 54-119925; (7) arylamine derivatives as disclosed in U.S. Pat. Nos. 3,567,450, 3,180,703, 3,240,597, 3,658,520, 4,232,103, 4,175,961 and 4,012,376, Japanese Patent Publications 49-35702 and 39-27577, Japanese Laid-Open Patent Applications 55-144250, 56-119132 and 56-22437, and West Germany Patent No. 1110518; (8) amino-substituted chalcone derivatives as disclosed in U.S. Pat. No. 3,526,501; (9) oxadiazole derivatives as disclosed in U.S. Pat. No. 3,257,203; (10) styryl anthracene derivatives as disclosed in Japanese Laid-Open Patent Application 56-46234, (11) fluorenone derivatives as disclosed in Japanese Laid-Open Patent Application 54-110837; (12) hydrazone derivatives as disclosed in U.S. Pat. No. 3,717,462, and Japanese Laid-Open Patent Applications 54-59143, 55-52063, 55-52064, 55-46760, 55-85495, 57-11350 and 57-148749; and (13) stilbene derivatives as disclosed in Japanese Laid-Open Patent Applications 61-210363, 61-228451, 61-14642, 61-72255, 62-47646, 62-36674, 62-10652, 62-30255, 60-93445, 60-94462, 60-174749 and 60-175052.

As the positive hole-transporting materials for the hole-transporting layer, tertiary amines used as compounds for a hole-transporting layer and porphyrin compounds used as compounds for positive charge injection, disclosed in Japanese Laid-Open Patent Application 63-295695, are particularly preferably employed.

As more preferable examples of the hole-transporting compounds for use in the present invention are those disclosed in Japanese Laid-Open Patent Applications 53-27033, 54-58445, 54-149634, 54-64299, 55-79450, 55-144250, 56-119132, 61-295558 and 61-98353, and U.S. Pat. No. 4,127,412. Specific examples of such hole-transporting compounds are shown in Table 5:

TABLE 5

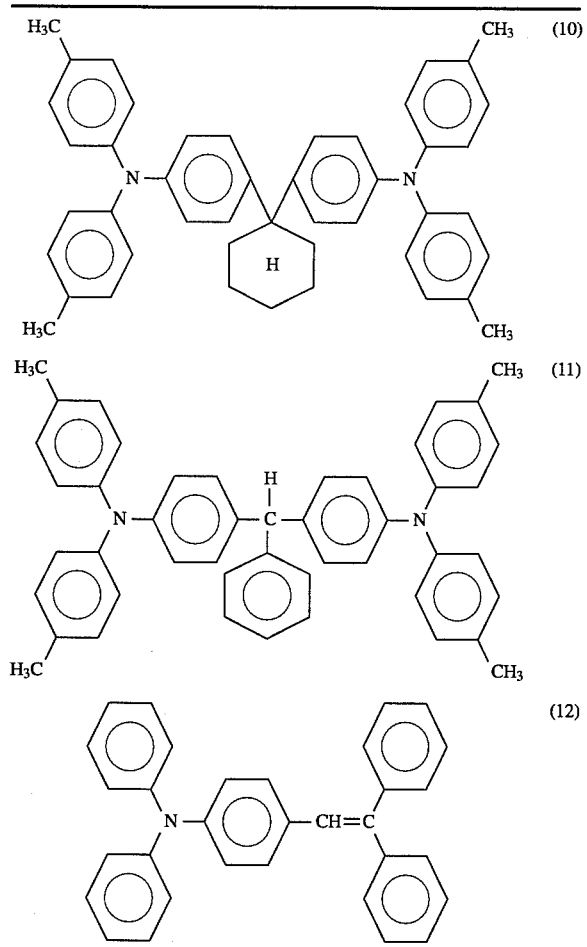

TABLE 5-continued

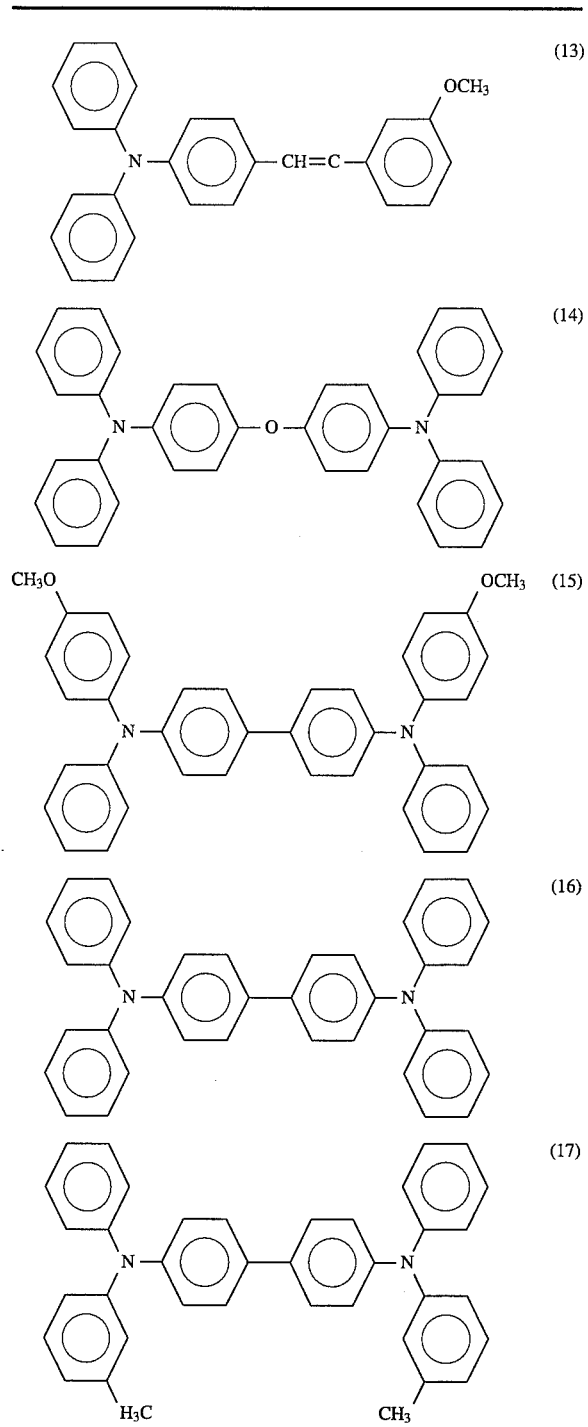

TABLE 5-continued

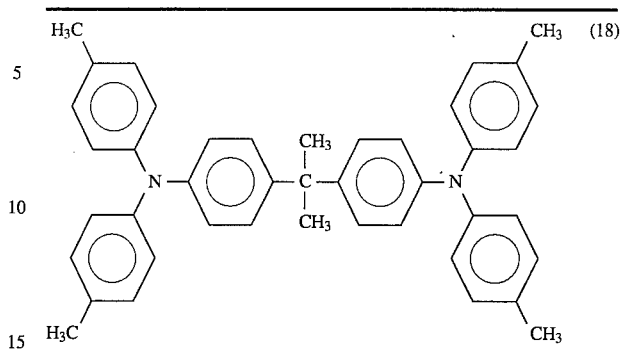

Each of the above hole-transporting materials is formed into a hole-transporting layer for use in the present invention. The hole-transporting layer may be either a single layer or a laminated layer comprising the above-mentioned hole-transporting material and another hole-transporting layer comprising a compound different from the above-mentioned hole-transporting materials.

Other features of this invention will become apparent in the course of the following description of exemplary embodiments, which are given for illustration of the invention and are not intended to be limiting thereof.

EXAMPLE I-1

On a glass substrate 1 provided with a indium-tin-oxide (ITO) positive electrode 2 having a surface resistivity of 20Ω/□, a hole-transporting layer 3c comprising the following triphenyl amine derivative represented by formula (19) with a thickness of 500Å, an electro-luminescent layer 3a comprising oxadiazole compound No. 2 shown in Table 1-(1) with a thickness of 500Å, and a negative electrode 4 comprising a magnesium-silver alloy with an atomic ratio of 10:1, with a thickness of 2000Å, were successively overlaid by the vacuum deposition method under the conditions that the substrate temperature was set at room temperature, and the degree of the vacuum set at $1 \times 10^{-6}$ torr, whereby an electro-luminescent device No. I-1 with a luminescent surface with a size of 2×2 mm according to the present invention with the structure as shown in FIG. 2 was fabricated:

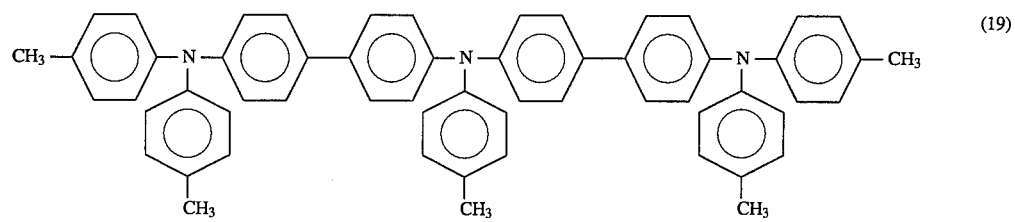

The thus fabricated electroluminescent device No. I-1 emitted clear blue light by the application of a drive voltage of 20 V or less.

EXAMPLES I-2 TO I-5

The procedure for fabrication of the electro-luminescent device No. I-1 in Example I-1 was repeated except that oxadiazole compound No. 2 shown in Table I-(1) employed in the electroluminescent layer of the electroluminescent device No. I-1 was replaced by the respective compounds shown in Table 6, whereby electroluminescent devices Nos. I-2 to I-5 according to the present invention were fabricated.

Each of the thus fabricated electroluminescent devices Nos. I-2 to I-5 emitted a clear light with the luminescent color as shown in Table 6 by the application of a drive voltage of 20 V or less.

TABLE 6

| Ex. No | Compound No. | Luminescent Color |
|--------|--------------|-------------------|
| I-2 | 13 in Table 1-(2) | blue |
| I-3 | 57 in Table 1-(8) | blue green |
| I-4 | 44 in Table 1-(5) | blue violet |
| I-5 | 49 in Table 1-(6) | blue green |

EXAMPLE I-6

On a glass substrate provided with an indium-tin-oxide (ITO) positive electrode having a surface resistivity of 20Ω/□, a hole-transporting luminescent layer comprising the following stilbene derivative represented by formula (20) with a thickness of 500Å, an electron-transporting layer comprising oxadiazole compound No. 25 shown in Table 1-(3) with a thickness of 500Å, and a negative electrode comprising a magnesium-silver alloy with an atomic ratio of 10:1, with a thickness of 2000Å, were successively overlaid by the vacuum deposition method, whereby an electroluminescent device No. I-6 according to the present invention was fabricated:

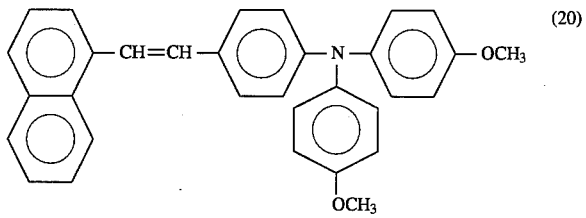

The thus fabricated electroluminescent device No. I-6 emitted light with a luminance of 230 cd/m² by the application of a drive voltage of 11.2 V at a current density of 30 mA/cm².

The electroluminescent device No. I-6 emitted a green light with an emission spectrum center at 520 nm.

EXAMPLE I-7

On a glass substrate provided with an indium-tin-oxide (ITO) positive electrode having a surface resistivity of 20Ω/□, a hole-transporting luminescent layer comprising the following diamine derivative represented by formula (21) with a thickness of 500Å, an electron-transporting layer comprising the oxadiazole compound No. 78 in Table 1-(10) with a thickness of 500Å, and a negative electrode comprising aluminum were successively overlaid by the vacuum deposition method under the conditions that the substrate temperature was set at room temperature, and the degree of the vacuum set at 0.7×10⁻⁶ torr, whereby an electroluminescent device No. I-7 according to the present invention was fabricated:

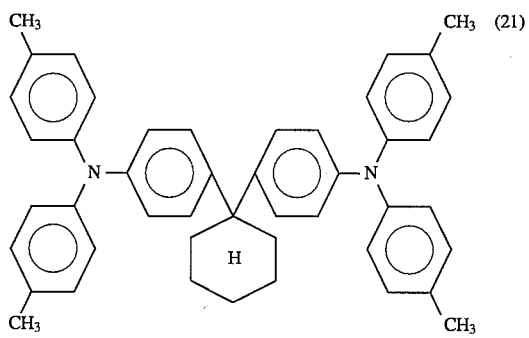

A direct electric source was connected to the thus fabricated electroluminescent device No. I-7 via a lead wire across the positive and negative electrodes. By the application of a drive voltage of 25 V at a current density of 50 mA/cm² to the electroluminescent device No. I-7, a white light emission comprising an exciplex component was observed, with the emission wavelength peaks thereof at 537 nm and 407 nm, and a luminance of 400 cd/m².

EXAMPLE I-8

On a glass substrate provided with an indium-tin-oxide (ITO) positive electrode having a surface resistivity of 20 Ω/, a hole transporting luminescent layer comprising the following compound represented by formula (22) with a thickness of 500Å, an electron-transporting layer comprising oxadiazole compound No. 78 shown in Table 1-(10) with a thickness of 500Å, and a negative electrode comprising a magnesium-silver alloy with an atomic ratio of 10:1, with a thickness of 2000Å, were successively overlaid by the vacuum deposition method, under the conditions that the substrate temperature was set at room temperature, and the degree of the vacuum set at 0.7×10⁻⁶ torr, whereby an electroluminescent device No. I-8 according to the present invention was fabricated:

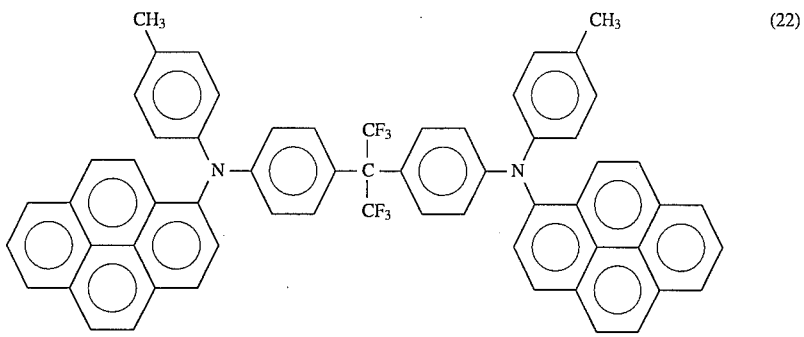

(22)

A direct electric source was connected to the thus fabricated electroluminescent device No. I-8 via a lead wire across the positive and negative electrodes. By the application of voltage of 20 V at a current density of 10 mA/cm$^2$ to the electroluminescent device No. I-8, a clear blue light emission with a luminance of 40 cd/m$^2$ was observed, with the emission wavelength peak at 464 nm.

EXAMPLE I-9

The procedure for fabrication of the electro-luminescent device No. I-8 in Example I-8 was repeated except that the compound of formula (22) employed in the hole-transporting luminescent layer in Example I-8 was replaced by the stilbene derivative of formula (20) employed in Example I-6, whereby an electroluminescent device No. I-9 according to the present invention was fabricated.

A direct electric source was connected to the thus fabricated electroluminescent device No. I-9 via a lead wire across the positive and negative electrodes. By the application of a voltage of 12.5 V at a current density of 100 mA/cm$^2$ to the electroluminescent device No. I-9, a clear green light emission with a luminance of 2000 cd/m$^2$ was observed with the emission wavelength peak at 515 nm.

After the electroluminescent device No. I-9 was continuously driven with the application of a constant current at a current density of 30 mA/cm$^2$ for one hour, the electroluminescent device No. I-9 still emitted light with a luminance of 100 cd/m$^2$.

COMPARATIVE EXAMPLE I-1

The procedure for fabrication of the electro-luminescent device No. I-9 in Example I-9 was repeated except that oxadiazole compound No. 78 employed in the electron-transporting layer in Example I-9 was replaced by the following compound represented by formula (23), whereby a comparative electroluminescent device No. I-1 was fabricated:

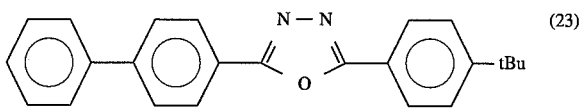

A direct electric source was connected to the thus fabricated comparative electroluminescent device No. I-1 via a lead wire across the positive and negative electrodes. As a result, a clear green light emission was observed in the same manner as in Example I-9, with the emission wavelength peak at 520 nm.

After the comparative electroluminescent device No. I-1 was continuously driven with the application of a constant current at a current density of 30 mA/cm$^2$ for one hour, no light emission was observed any longer.

COMPARATIVE EXAMPLE I-2

The procedure for fabrication of the electro-luminescent device No. I-9 in Example I-9 was repeated except that oxadiazole compound No. 78 employed in the electron-transporting layer in Example I-9 was replaced by the following compound represented by formula (24), whereby a comparative electroluminescent device No. I-2 was fabricated:

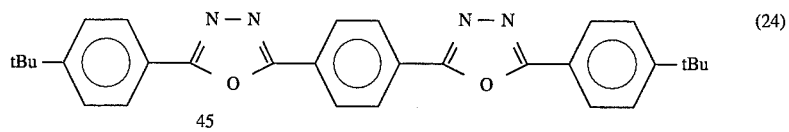

A direct electric source was connected to the thus fabricated comparative electroluminescent device No. I-2 via a lead wire across the positive and negative electrodes. As a result, a clear green light emission was observed in the same manner as in Example I-9, with the emission wavelength peak at 522 nm.

After the comparative electroluminescent device was continuously driven with the application of a constant current at a current density of 30 mA/cm$^2$ for one hour, the luminance of the light emitted by the comparative electroluminescent device No. I-2 was 50 cm/m$^2$ or less.

EXAMPLE I-10

The procedure for fabrication of the electro-luminescent device No. I-8 in Example I-8 was repeated except that the compound represented by formula (22) employed in the hole-transporting luminescent layer in Example I-8 was replaced by the following compound represented by formula (25), whereby an electro-luminescent device No. I-10 according to the present invention was fabricated:

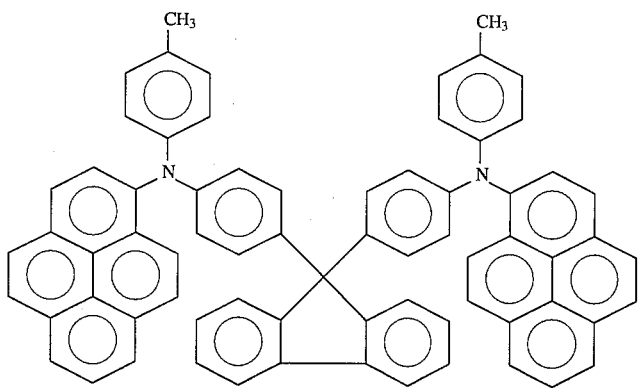

(25)

A direct electric source was connected to the thus fabricated comparative electroluminescent device No. I-10 via a lead wire across the positive and negative electrodes. As a result, a light emission with a luminance of 8 cd/m² was observed with the application of a constant current at a current density of 30 mA/cm².

After the electroluminescent device No. I-10 was continuously driven with the application of a constant current at a current density of 30 mA/cm² for one hour, the electroluminescent device No. I-10 emitted a light with a luminance of 215 cd/m² with the application of a drive voltage of 24 V. It was observed that the luminous efficiency was increased with time.

EXAMPLE I-11

On a glass substrate provided with an indium-tin-oxide (ITO) positive electrode having a surface resistivity of 20Ω/58 , a hole-transporting layer comprising the triphenyl amine derivative of formula (19) employed in Example I-1 with a thickness of 400Å, an electroluminescent layer comprising the following compound represented by formula (26) with a thickness of 150Å, an electron-transporting layer comprising compound No. 78 shown in Table 1-(10) with a thickness of 500Å, and a negative electrode comprising a magnesium-silver alloy with an atomic ratio of 10:1, with a thickness of 2000Å, were successively overlaid by the vacuum deposition method, whereby an electroluminescent device No. I-11 according to the present invention was fabricated:

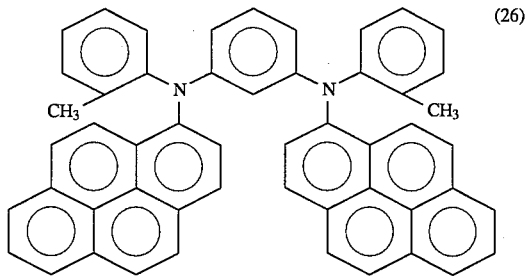

(26)

When a direct voltage of 6.4 V at a current density of 30 mA/cm² was applied to the thus fabricated electro-luminescent device No. I-11, a light emission with a luminance of 640 cd/m² was observed, with the emission wavelength peak at 475 nm, based on the emission from the electroluminescent layer.

The electroluminescent device No. I-11 was continuously driven with the application of a constant current at a current density of 30 mA/cm² for one hour. Even after the one-hour driving, the light emission with a luminance of 300 cd/m² was maintained.

COMPARATIVE EXAMPLE I-3

The procedure for fabrication of the electro-luminescent device No. I-11 in Example I-11 was repeated except that oxadiazole compound No. 78 employed in the electron-transporting layer in Example I-11 was replaced by the compound of formula (23) employed in Comparative Example I-1, whereby a comparative electroluminescent device No. I-3 was fabricated.

A direct electric source was connected to the thus fabricated comparative electroluminescent device No. I-3 via a lead wire across the positive and negative electrodes. As a result, a clear blue green light emission was observed in the same manner as in Example I-9, with the emission wavelength peak at 485 nm.

After the comparative electroluminescent device No. I-3 was continuously driven with the application of a constant current at a current density of 30 mA/cm² for one hour, the luminance of the light emission was 20 cd/m² or less.

COMPARATIVE EXAMPLE I-4

The procedure for fabrication of the electro-luminescent device No. I-11 in Example I-11 was repeated except that oxadiazole compound No. 78 employed in the electron-transporting layer in Example I-11 was replaced by the compound of formula (24) employed in Example I-2, whereby a comparative electroluminescent device No. I-4 was fabricated.

A direct electric source was connected to the thus fabricated comparative electroluminescent device No. I-4 via a lead wire across the positive and negative electrodes. As a result, a clear blue green light emission was observed in the same manner as in Example I-9, with the emission wavelength peak at 483 nm.

After the comparative electroluminescent device No. I-4 was continuously driven with the application of a constant current at a current density of 30 mA/cm² for one hour, the luminance of the light emission was 60 cd/m² or less.

COMPARATIVE EXAMPLE I-5

The procedure for fabrication of the electro-luminescent device No. I-11 in Example I-11 was repeated except that oxadiazole compound No. 78 employed in the electron-transporting layer in Example I-11 was replaced by the following compound represented by formula (27), whereby a comparative electroluminescent device No. I-5 was fabricated:

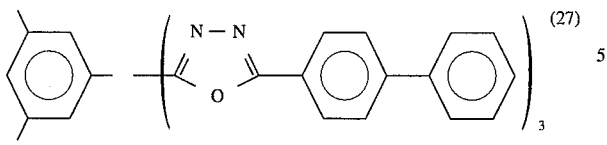

A direct electric source was connected to the thus fabricated comparative electroluminescent device No. I-5 via a lead wire across the positive and negative electrodes. As a result, a green light emission was observed with the emission wavelength peak at 499 nm, which was different from the emission wavelength peak obtained in Example I-11.

After the comparative electroluminescent device No. I-5 was continuously driven with the application of a constant current at a current density of 30 mA/cm$^2$, the luminance obtained was as small as 105 cd/m$^2$, indicating that the luminous efficiency of the comparative electro-luminescent device No. I-5 was decreased in comparison with the case where oxadiazole compound No. 78 was employed in the electron-transporting layer.

EXAMPLES I-12 TO I-22

The procedure for fabrication of the electro-luminescent device No. 11 in Example I-11 was repeated except that the compound of formula (26) employed in the electroluminescent layer in Example I-11 was replaced by the compounds of formulas (28) to (33) shown in Table 7, the compound of formula (25) and the compounds of formulas (34) to (37) shown in Table 7, whereby the respective electroluminescent devices Nos. 12 to 22 according to the present invention in Examples I-12 to I-22 were fabricated.

The electroluminescent devices Nos. 12 to 22 showed the electroluminescent characteristics as shown in Table 8, when driven by the application of the respective D.C. voltages thereto shown in Table 8.

TABLE 7

| Ex. No. | Compound No. | X | R |
|---|---|---|---|
| I-12 | (28) | phenyl | phenyl-OCH$_3$ (ortho) |
| I-13 | (29) | phenyl | phenyl-CH$_3$ |
| I-14 | (30) | phenyl | phenyl-OCH$_3$ |
| I-15 | (31) | phenyl | phenyl-nBu |
| I-16 | (32) | phenyl | phenyl-iso-Bu |
| I-17 | (33) | methyl-substituted phenyl | phenyl-Sec-Bu |

TABLE 7-continued

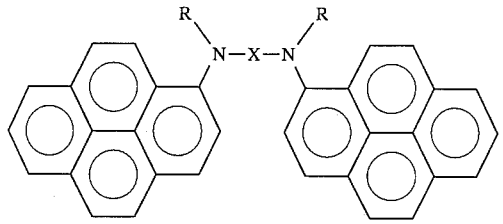

| Ex. No. | Compound No. | X | R |
|---------|--------------|---|---|
| I-19 | (34) | (m-phenylene) | (phenyl-OCH$_3$) |
| I-20 | (35) | (biphenylene) | (phenyl-CH$_3$) |
| I-21 | (36) | (m-phenylene) | (phenyl-t-Bu) |
| I-22 | (37) | (m-phenylene) | (phenyl with CH$_3$) |

TABLE 8

| Ex. No. | Compound No. | Voltage* (V) | Luminance* (cd/m$^2$) | Wavelength at Luminescent Peak (nm) |
|---------|--------------|--------------|------------------------|--------------------------------------|
| I-12 | (28) | 6.2 | 400 | 494 |
| I-13 | (29) | 7.0 | 340 | 487 |
| I-14 | (30) | 6.8 | 750 | 512 |
| I-15 | (31) | 7.2 | 610 | 485 |
| I-16 | (32) | 6.9 | 375 | 477 |
| I-17 | (33) | 6.2 | 620 | 480 |
| I-18 | (25) | 6.7 | 670 | 512 (485: subpeak) |
| I-19 | (34) | 9.5 | 561 | 488 |
| I-20 | (35) | 8.6 | 420 | 508 |
| I-21 | (36) | 11.2 | 800 | 480 |
| I-22 | (37) | 7.3 | 600 | 487 |

*Current Density J = 30 mA/cm$^2$

TABLE 9

| Ex. No. | Compound No. | Voltage* (V) | Luminance* (cd/m$^2$) |
|---------|--------------|--------------|------------------------|
| I-23 | 23 | 12.0 | 10 |
| I-24 | 25 | 18.0 | 20 |
| I-25 | 27 | 20.0 | 15 |
| I-26 | 26 | 16.0 | 25 |
| I-27 | 79 | 10.2 | 640 |
| I-28 | 68 | 11.0 | 540 |
| I-29 | 89 | 10.5 | 670 |
| I-30 | 71 | 12.6 | 330 |
| I-31 | 91 | 12.5 | 840 |
| I-32 | 92 | 13.5 | 568 |
| I-33 | 93 | 14.3 | 420 |
| I-34 | 70 | 12.8 | 660 |

*Current Density J = 30 mA/cm$^2$

EXAMPLES I-23 TO I-34

The procedure for fabrication of the electro-luminescent device No. I-11 in Example I-11 was repeated except that oxadiazole compound No. 78 employed in the electron-transporting layer in Example I-11 was replaced by the respective oxadiazole compounds shown in Table 9, whereby electroluminescent devices Nos. I-23 to I-34 according to the present invention in Examples I-23 to I-34 were fabricated.

When the respective D.C. voltage as shown in Table 9 was applied to the electroluminescent devices Nos. I-23 to I-34 to drive the same, the electroluminescent devices Nos. I-23 to I-34 showed the electroluminescent characteristics as shown in Table 9.

EXAMPLE II-1

Synthesis of 2,2-bis(4-carbazoylphenyl)hexafluoropropane of formula (VII-1)

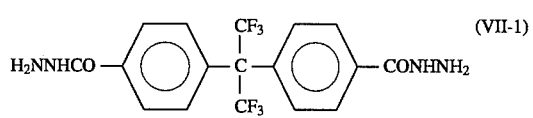

4.20 g of 2,2-bis(4-methoxycarbonylphenyl) hexafluoropropane was added to 10.01 g of anhydrous hydrazine. This reaction mixture was heated to about 90° C. for 3 hours. The reaction mixture was then cooled to room temperature and then poured into about 200 ml of ice water. As a result, a white precipitate was produced. The thus obtained white precipitate was separated by filtration, washed with water and dried, whereby a product was obtained in a yield of 3.90 g (93.5%). The thus obtained produce was recrystallized from a mixed solvent of N,N-dimethyl-formamide and water, whereby colorless crystals in the form of plates were obtained in a yield of 3.35 g (79.7%).

The melting point of the above obtained colorless crystals was 269.0° to 271.0° C.

An infrared absorption spectrum (Kbr spectrum) of the above colorless crystals indicated characteristic absorption peaks of $\upsilon$N—H at 3330 cm$^{-1}$ and 3230 cm$^{-1}$, and of $\upsilon$C=O at 1680 cm$^{-1}$ and 1640 cm$^{-1}$.

The results of the elemental analysis of the colorless crystals, calculated based on the formula of $C_{17}H_{14}N_4O_2F_6$, were as follows:

|  | % C | % H | % N |
|---|---|---|---|
| Found | 48.56 | 3.15 | 13.40 |
| Calculated | 48.58 | 3.36 | 13.33 |

From the above results, it was confirmed that the above colorless crystals were 2,2-bis(4-carbazoylphenyl) hexafluoropropane.

EXAMPLE II-2

Synthesis of Compound of Formula (VII-3-A)

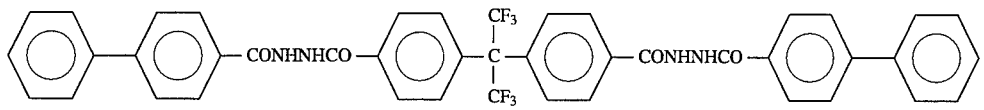
(VII-3-A)

4.77 g of p-phenyl benzoyl chloride of formula (VII-2-A) was dissolved in 60 ml of pyridine over a period of about 20 minutes at room temperature.

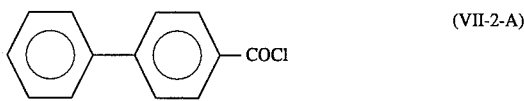
(VII-2-A)

4.20 g of 2,2-bis(4-carbazoylphenyl)hexafluoropropane obtained in Example II-1 was added to the thus pyridine solution of p-phenyl benzoly chloride.

Subsequently, the mixture was allowed to react at room temperature for 15 minutes and then at about 100° C. for 3 hours. The reaction mixture was cooled to room temperature and poured into about 400 ml of ice water. As a result, a precipitate was produced. The thus obtained precipitate was separated by filtration, washed with water, dried, and recrystallized from a mixed solvent of N,N-dimethylformamide and ethanol twice, whereby a white product in the form of powder was obtained in a yield of 6.91 g (88.5%).

The melting point of the above obtained white product was 217° to 221.0° C.

An infrared absorption spectrum (Kbr spectrum) of the above white product indicated characteristic absorption peaks of 1-substituted phenyl nucleus at 740 cm$^{-1}$ and 700 cm$^{-1}$ and of $\upsilon$N—H at 3250 cm$^{-1}$.

The results of the elemental analysis of this white product, calculated based on the formula of $C_{43}H_{20}N_4O_4F_6$, were as follows:

|  | % C | % H | % N |
|---|---|---|---|
| Found | 65.65 | 3.56 | 7.07 |
| Calculated | 66.15 | 3.87 | 7.18 |

From the above results, it was confirmed that the above white product was the compound of formula (VII-3-A).

EXAMPLES II-3 TO II-14

The procedure for synthesizing the compound of formula (VII-3-A) in Example II-2 was repeated except that the compound of formula (VII-2-A) employed in Example II-2 was replaced by the respective compounds of formula (VII-2) as shown in Table 10, whereby compounds of formula (VII-3) were obtained.

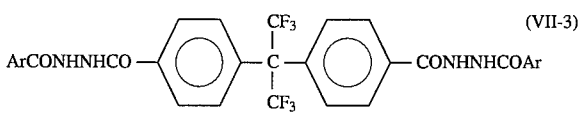
(VII-3)

TABLE 10
ArCOX      (VII-2)
| Example No. | Formula (VII-2) Ar | X | Formula (VII-3) Yield | Absorption Peak of IR Spectrum |
|---|---|---|---|---|
| II-3 | 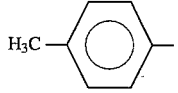 | —Cl | 89.7% | 1640 cm$^{-1}$ |
| II-4 | 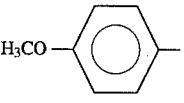 | —Cl | 52.3% | 1660 cm$^{-1}$ |
| II-5 | 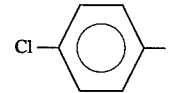 | —Cl | 76.6% | 1700 cm$^{-1}$<br>1660 cm$^{-1}$ |
| II-6 | 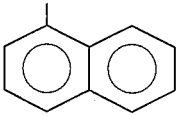 | —Cl | ~100% | 1680 cm$^{-1}$<br>1660 cm$^{-1}$ |
| II-7 | 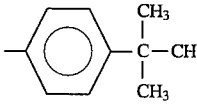 | —Cl | ~100% | 2960 cm$^{-1}$<br>1640 cm$^{-1}$ |
| II-8 | 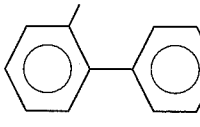 | —Cl | 87.95% | 3225 cm$^{-1}$<br>1650 cm$^{-1}$ |
| II-9 | 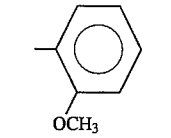 | —Cl | 89.65% | 3280 cm$^{-1}$<br>1630 cm$^{-1}$ |
| II-10 | 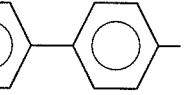 | —Cl | 95.84% | 3250 cm$^{-1}$<br>1640 cm$^{-1}$ |
| II-11 | 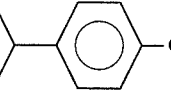 | —Cl | 93.65% | 3250 cm$^{-1}$<br>1640 cm$^{-1}$ |
| II-12 | 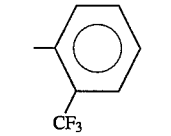 | —Cl | >100% | 3200 cm$^{-1}$<br>1670 cm$^{-1}$ |
| II-13 | 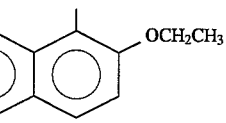 | —Cl | >100% | 3220 cm$^{-1}$<br>1660 cm$^{-1}$ |

TABLE 10-continued

ArCOX   (VII-2)

| Example No. | Formula (VII-2) Ar | X | Yield | Formula (VII-3) Absorption Peak of IR Spectrum |
|---|---|---|---|---|
| II-14 | 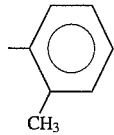 | —Cl | 88.0% | 3250 cm$^{-1}$<br>1660 cm$^{-1}$ |

EXAMPLE II-15

Synthesis of Oxadiazole Compound No. 78 in Table 1-(10)

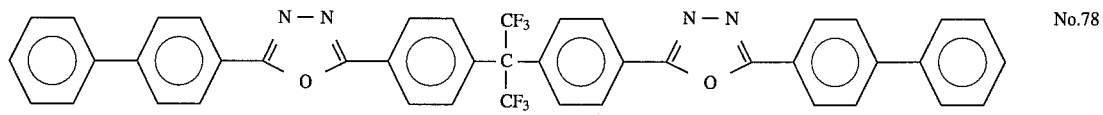

A mixture of 1.95 g of the compound of formula (VII-3-A) obtained in Example II-2 and 20 ml of phosphorus oxychloride was refluxed for 34 hours. The mixture was cooled to room temperature and poured into ice water, whereby a white precipitate was obtained. The thus obtained white precipitate was separated by filtration, washed with water, and dried, so that 1.94 g of a white powder was obtained.

The thus obtained white powder was recrystallized from N,N-dimethylformamide twice, subjected to silica gel-chloroform column chromatography for purification, and then recrystallized from dioxane, whereby white highly fluorescent crystals were obtained in a yield of 0.59 g (31.7%).

The melting point of the above obtained white crystals was 300° C. or more.

Figure 5:
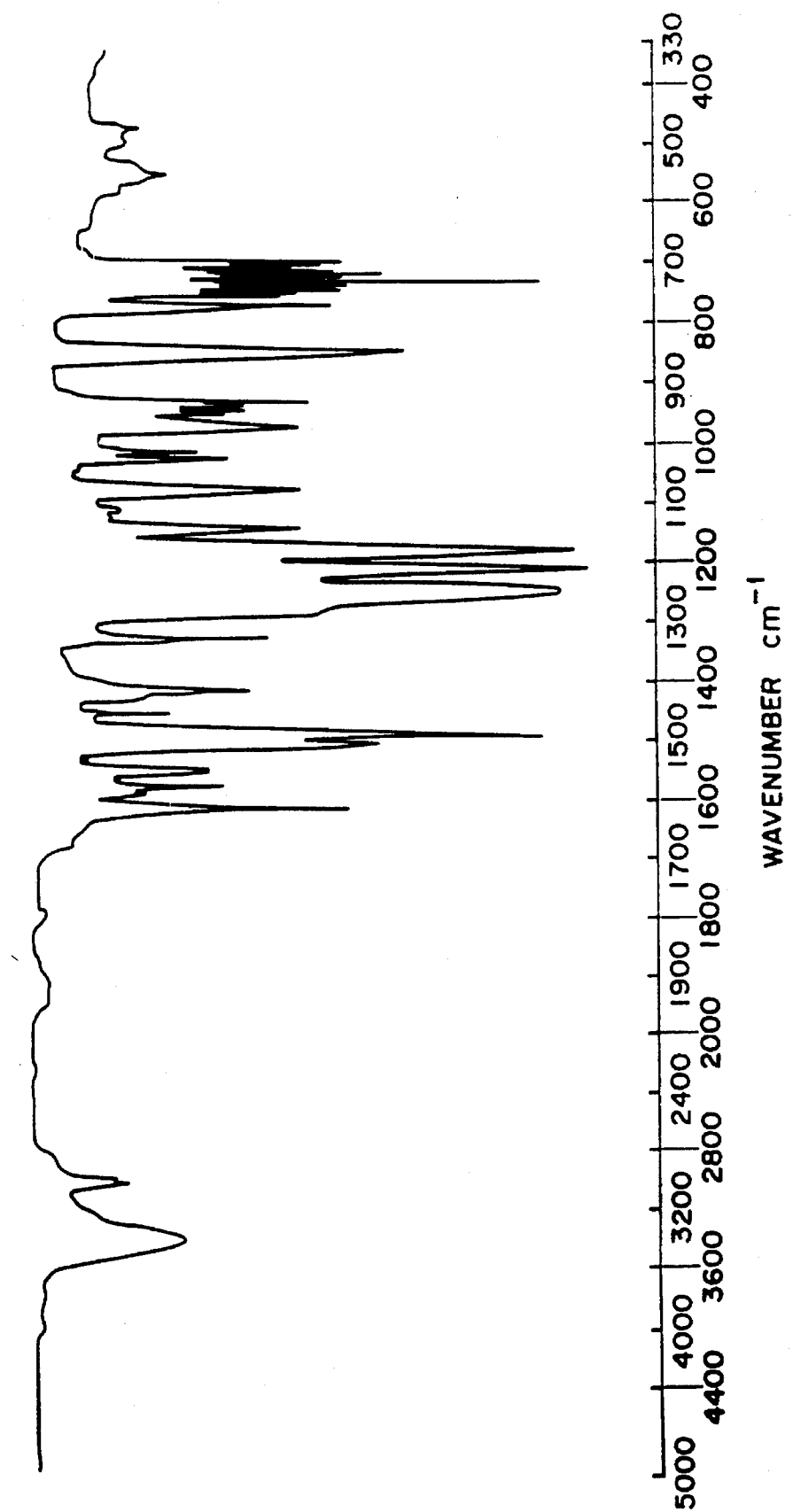
FIG. 5 is an infrared absorption spectrum (KBr tablet) of oxadiazole compound No. 78 shown in Table 1-(10)

An infrared absorption spectrum (Kbr spectrum) of the white crystals is shown in FIG. 5, by which the disappearance of the characteristic absorption peaks of υN—H and υC=O was confirmed.

The results of the elemental analysis of the white crystals, calculated based on the formula of $C_{43}H_{26}N_4O_2F_6$ were as follows.

|  | % C | % H | % N | % F |
|---|---|---|---|---|
| Found | 69.12 | 3.25 | 7.53 | 15.4 |
| Calculated | 69.35 | 3.52 | 7.52 | 15.31 |

From the above results, it was confirmed that the above crystals were Oxadiazole Compound No. 78 in Table 1-(10).

EXAMPLE II-16

Synthesis of Oxadiazole Compound No. 68 in Table 1-(10)

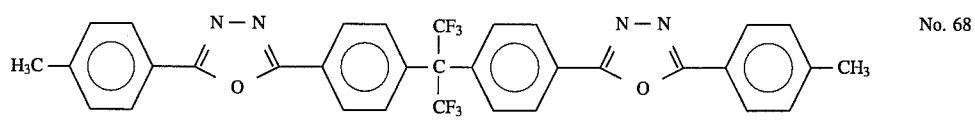

A mixture of 6.56 g of the compound of the following formula (VII-3-B) obtained in Example II-3 and 80 ml of o-dichlorobenzene was heated at about 165° C.:

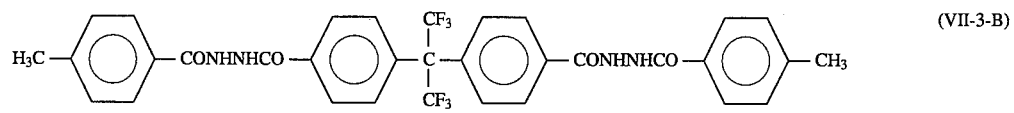

7.14 g of thionyl chloride was added dropwise to the above reaction mixture, with vigorously stirring, over a period of about 1 hour at about 165° C. Even after the completion of the dropwise addition of the thionyl chloride, the mixture was allowed to react at the same temperature for 3 hours and was then cooled to room temperature.

Subsequently, the thionyl chloride still remaining in the reaction mixture was decomposed with the addition of water thereto. The reaction mixture was separated into an aqueous layer and an organic layer. The organic layer was washed with water three times, and dried over anhydrous magnesium sulfate. Thereafter, the solvent was distilled away. As a result, a light yellow powder was obtained.

The thus obtained light yellow powder was washed with methanol and dried, whereby 4.51 g of a product was obtained. This product was then subjected to silica gel-chloroform column chromatography for purification, and recrystallized from toluene twice, whereby white high fluorescent crystals were obtained in a yield of 2.36 g (38.0%).

The melting point of the above obtained white fluorescent crystals was 260.5° C. to 261.5° C.

By an infrared absorption spectrum (Kbr spectrum) of the above white crystals, the disappearance of the characteristic absorption peaks of $\nu$N—H and $\nu$C=O was confirmed.

The results of the elemental analysis of this product, calculated based on the formula of $C_{33}H_{22}N_4O_2F_6$, were as follows:

|  | % C | % H | % N | % F |
|---|---|---|---|---|
| Found | 63.55 | 3.33 | 9.25 | 18.2 |
| Calculated | 63.87 | 3.57 | 9.03 | 18.37 |

From the above results, it was confirmed that the above product was Oxadiazole Compound No. 68 in Table 1-(10).

EXAMPLE II-17

Synthesis of Oxadiazole Compound No. 79 in Table 1-(10)

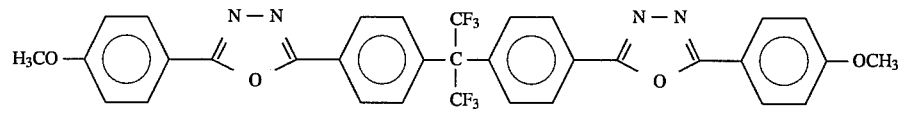
No. 79

A mixture of 4.41 g of the compound of the following formula (VII-3-C) obtained in Example II-4 and 50 ml of monochlorobenzene was refluxed:

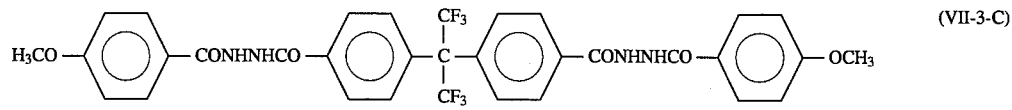
(VII-3-C)

4.62 g of thionyl chloride was added dropwise to the mixture with the above refluxing temperature maintained, with vigorously stirring, over a period of about 30 minutes. Even after the completion of the dropwise addition of the thionyl chloride, the mixture was refluxed to react for about 6 hours to proceed with the reaction, and then cooled to room temperature. 100 ml of methanol was added thereto. As a result, a white precipitate was produced. The white precipitate was separated by filtration, washed with water, and dried. Thus, 2.48 g of a white powder was obtained.

The thus obtained white powder was subjected to silica gel-chloroform column chromatography for purification, and recrystallized from N,N-dimethyl-formamide twice, whereby white highly fluorescent crystals were obtained in a yield of 1.88 g (45.0%).

The melting point of the above obtained white crystals was 296.0° C. to 297.2° C.

An infrared absorption spectrum (KBr spectrum) of the above crystals indicated that the disappearance of the characteristic absorption peaks of $\nu$N—H and $\nu$C=O.

The results of the elemental analysis of this crystals, calculated based on the formula of $C_{33}H_{22}N_4O_4F_6$, were as follows:

|  | % C | % H | % N | % F |
|---|---|---|---|---|
| Found | 60.41 | 3.09 | 8.35 | 17.6 |
| Calculated | 60.74 | 3.40 | 8.59 | 17.47 |

From the above results, it was confirmed that the above crystals were Oxadiazole Compound No. 79 in Table 1-(10).

EXAMPLES II-18 TO II-26

Compounds represented by formula (VII-3) were subjected to dehydration to form the rings in the same manner as in Examples II-15 to II-17, whereby oxadiazole compounds shown in Table 11 were obtained.

Ar of each compound of formula (VII-3), the yield, melting point, and the elemental analysis thereof are also shown in Table 11.

TABLE 11

Figure 6:
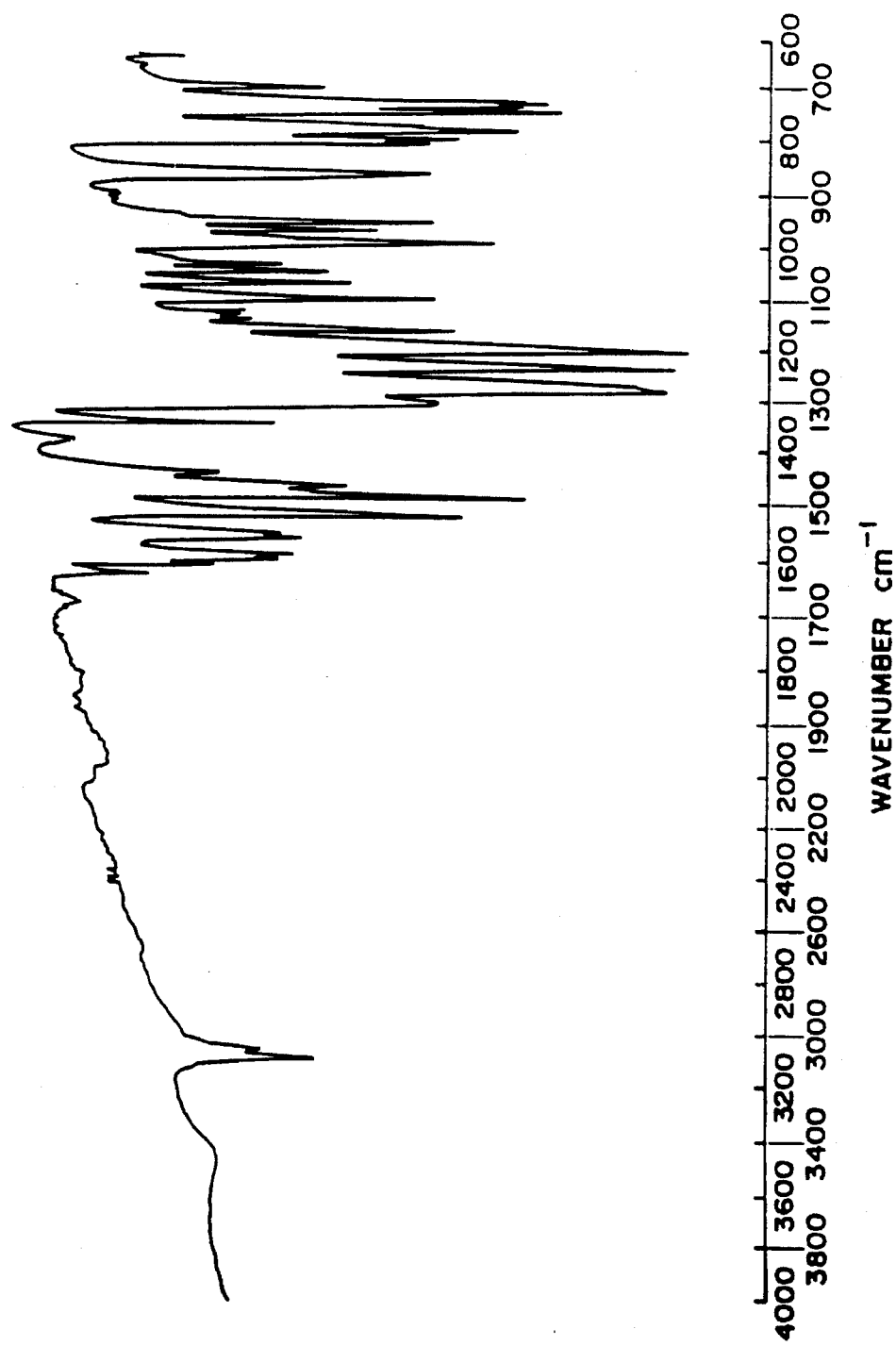
FIG. 6 is an infrared absorption spectrum (KBr tablet) of oxadiazole compound No. 92 shown in Table 1-(10)
Figure 7:
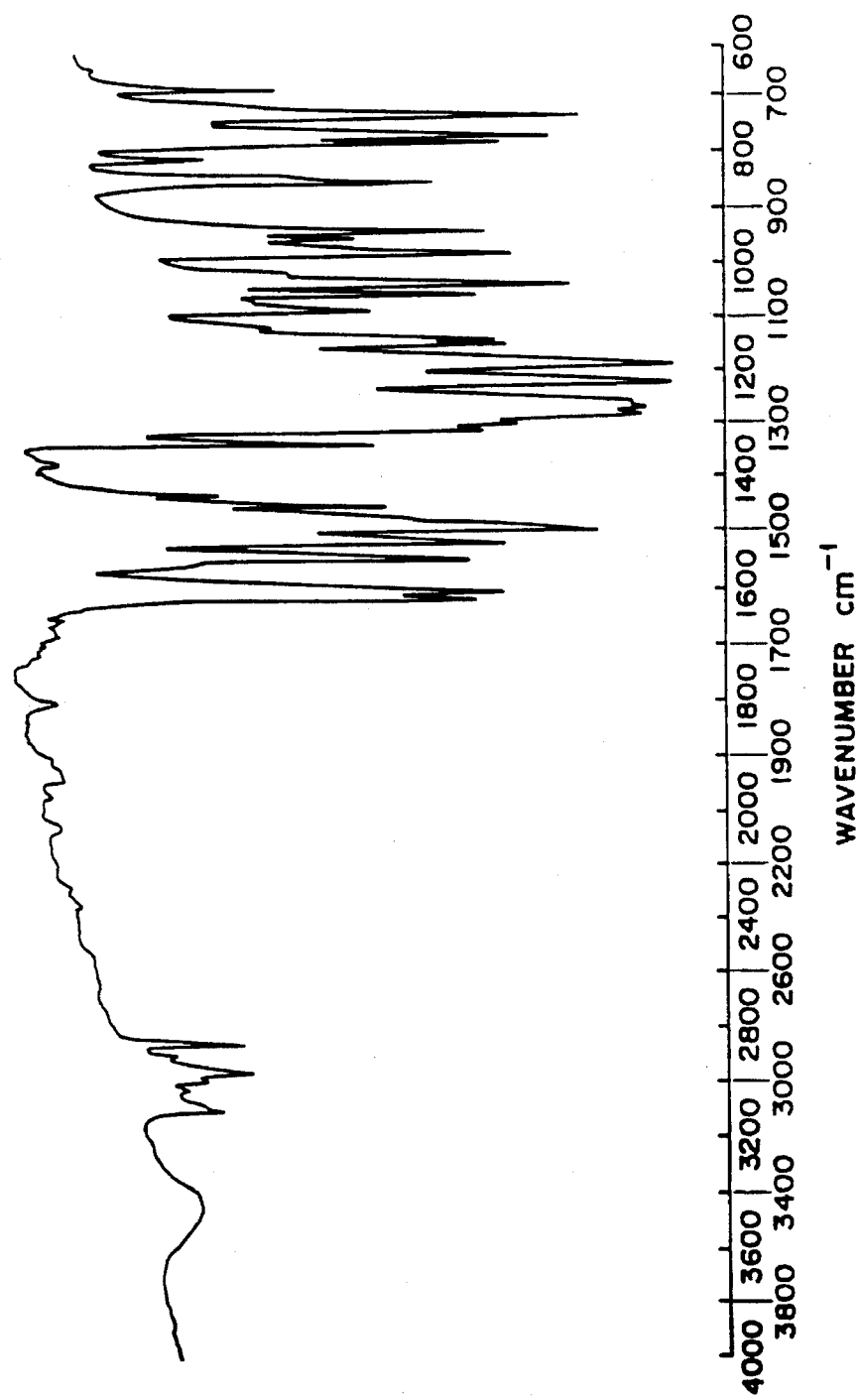
FIG. 7 is an infrared absorption spectrum (KBr tablet) of oxadiazole compound No. 93 shown in Table 1-(10)
Figure 8:
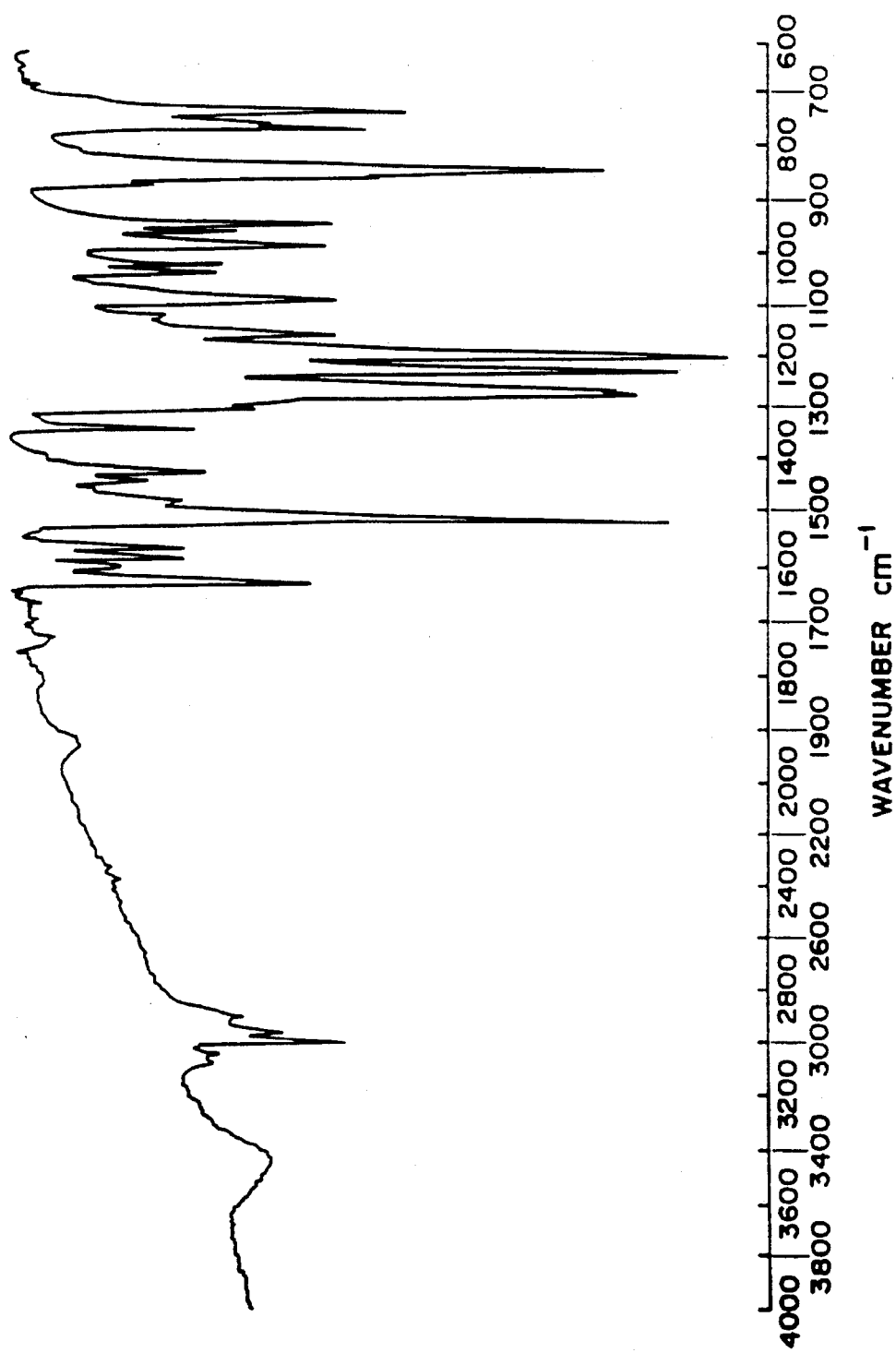
FIG. 8 is an infrared absorption spectrum (KBr tablet) of oxadiazole compound No. 94 shown in Table 1-(10)
Figure 9:
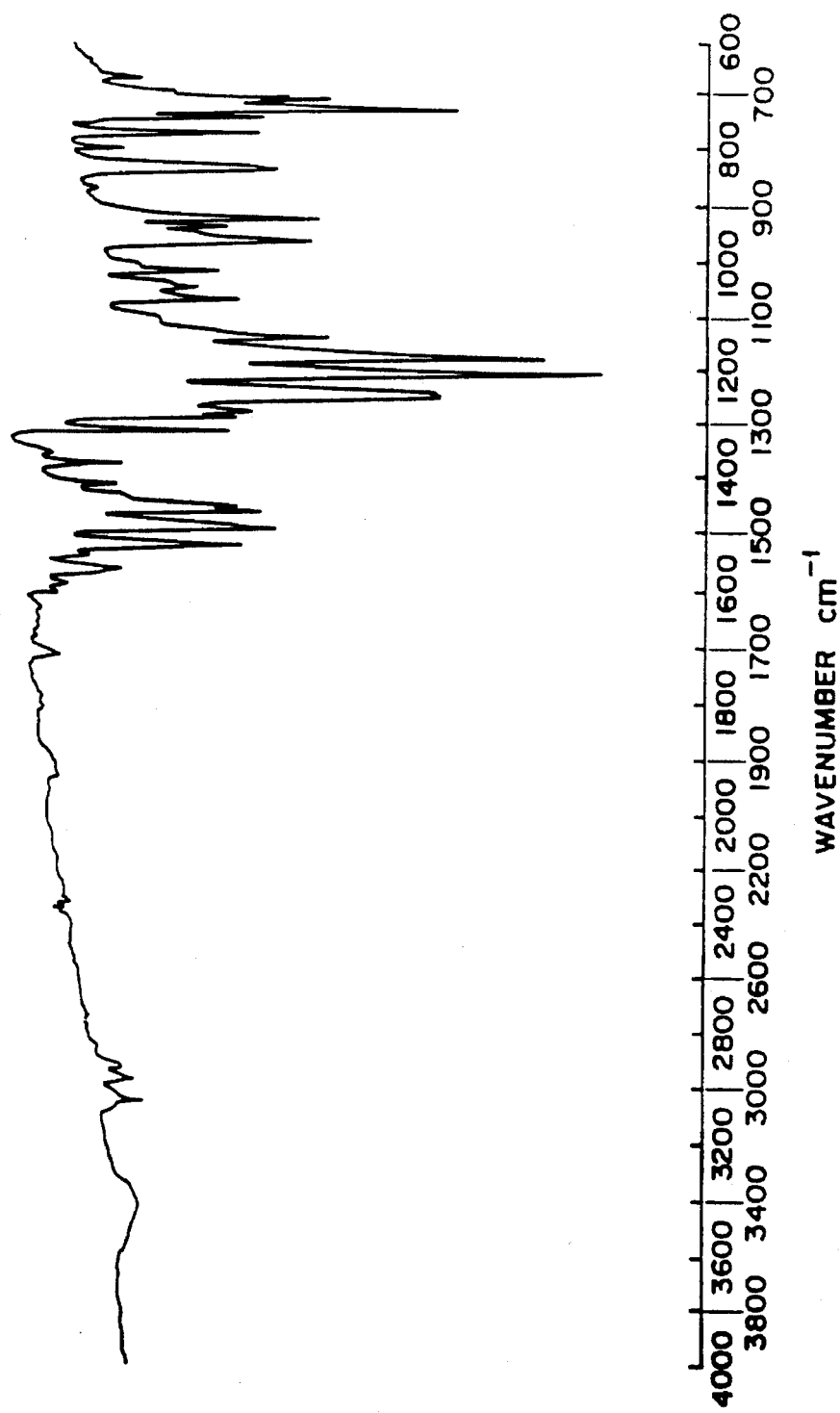
FIG. 9 is an infrared absorption spectrum (KBr tablet) of oxadiazole compound No. 70 shown in Table 1-(10)

| Ex. No. | Synthesized Compound No. | Formula (VII-3) Ar | Yield (%) | Melting Point (°C.) | Elemental Analysis Found (Calculated) | | | IR Absorption Spectrum |
|---|---|---|---|---|---|---|---|---|
| | | | | | % C | % H | % N | |
| II-18 | 71 | —C₆H₄—Cl | 12.1 | 260.0–261.0 | 56.57 (56.29) | 2.15 (2.44) | 8.56 (8.47) | — |
| II-19 | 89 | 1-naphthyl | 11.3 | 232.0–233.0 | 67.68 (67.63) | 3.23 (3.20) | 8.02 (8.09) | — |
| II-20 | 80 | —C₆H₄—C(CH₃)₃ | 31.2 | 193.0–194.0 | 66.51 (66.47) | 4.80 (4.86) | 7.95 (7.95) | — |
| II-21 | 92 | 2-phenylphenyl | 39.7 | 183.5–184.5 | 69.42 (69.07) | 3.64 (3.91) | 7.54 (7.49) | FIG. 6 |
| II-22 | 93 | 2-methoxyphenyl | 8.33 | 191.5–193.0 | 61.45 (60.74) | 3.58 (3.40) | 8.36 (8.59) | FIG. 7 |
| II-23 | 94 | 4'-ethylbiphenyl | 52.17 | 243.0–244.0 | 70.57 (70.49) | 4.54 (4.78) | 6.99 (7.00) | FIG. 8 |
| II-24 | 95 | 4'-propylbiphenyl | 45.5 | 208.0–210.0 | 71.33 (71.01) | 4.55 (4.62) | 6.70 (6.76) | — |
| II-25 | 97 | 2-ethoxy-1-naphthyl | 4.37 | 175.5–176.5 | 66.14 (66.15) | 3.78 (3.87) | 7.20 (7.18) | — |
| II-26 | 70 | 2-methylphenyl | 7.25 | 222.5–223.5 | 63.98 (63.87) | 3.66 (3.57) | 8.71 (9.03) | FIG. 9 |

EXAMPLE II-27

Synthesis of 5-(2-naphthyl)-1H-tetrazole represented by formula (VII-7-A)

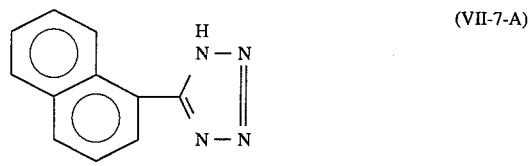
(VII-7-A)

A mixture of 10 g of 2-cyanonaphthalene, 10.61 g of sodium azide, and 7.67 g of lithium chloride was placed in a reaction vessel, and 240 ml of 2-methoxyethanol serving as a solvent was added thereto. The above mixture was refluxed with stirring for 80 hours. The mixture was cooled to room temperature, and 500 ml of water was added to the mixture.

Thereafter, an insoluble matter was removed from the mixture and 13.5 ml of 35% hydrochloric acid was added dropwise thereto with stirring, whereby a product was separated out. The thus obtained product was filtered off, and washed with water, so that crude product was obtained in a yield of 12.17 g (95.0%).

The thus obtained crude product was recrystallized from a mixed solvent of 340 ml of toluene and 140 ml of 1,4-dioxane, whereby colorless crystals in the form of needles were obtained in a yield of 9.14 g (71.4%. The decomposition point of the colorless crystals was 205.5° C. to 205.8° C.

An infrared absorption spectrum of the above colorless crystals indicated a characteristic broad peak of N—H stretching vibration of tetrazole at 3000 cm$^{-1}$ to 2400 cm$^{-1}$.

EXAMPLE II-28

Synthesis of Oxadiazole Compound No. 91 in Table 1-(10)

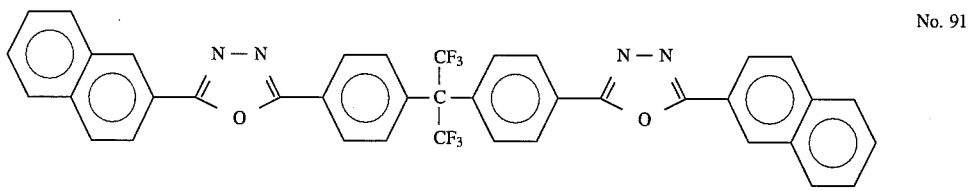

No. 91

A mixture of 2.0 g of the 5-(2-naphthyl)-1H-tetrazole obtained Example II-27 and 2.18 g of 2,2-bis(4-chloroformylphenyl)hexafluoropropane was placed in a reaction vessel, and 50 ml of pyridine serving as a solvent was added thereto. The above mixture was refluxed with stirring for 4 hours.

Subsequently, the mixture was cooled to room temperature, and then 50 ml of methanol was added to the mixture, whereby a product was completely separated out. The thus obtained product was filtered off, and washed with methanol, so that a crude product was obtained in a yield of 3.03 g (85.8%).

The thus obtained crude product was recrystallized from 120 ml of N,N-dimethylformamide, whereby colorless crystals in the form of spherulites was obtained in a yield of 2.99 g (84.7%).

The melting point of the above obtained colorless crystals was 300° C. or more.

Figure 10:
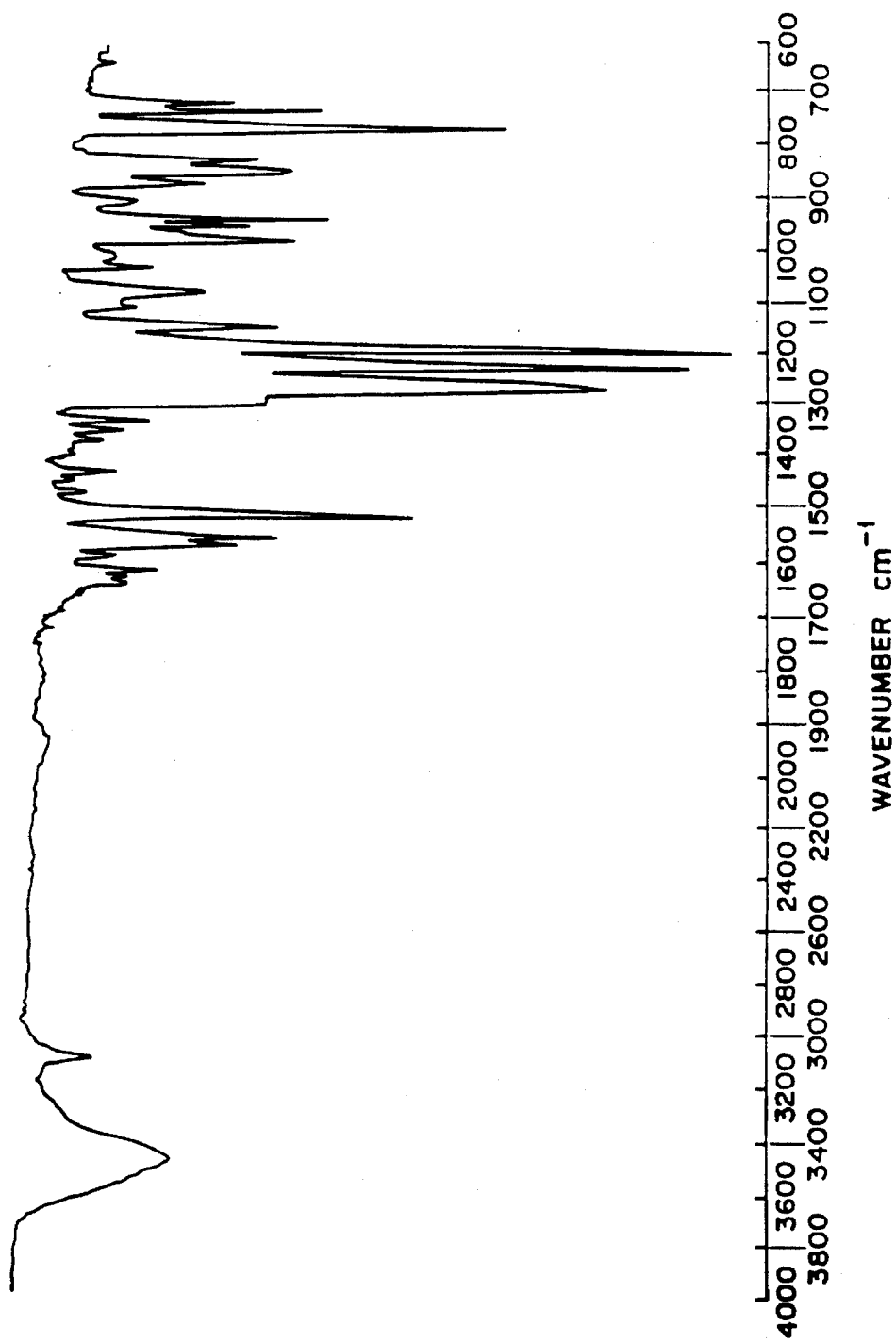
FIG. 10 is an infrared absorption spectrum (KBr tablet) of oxadiazole compound No. 91 shown in Table 1-(10)

An infrared absorption spectrum (KBr tablet) of the colorless crystals is shown in FIG. 10.

The results of the analysis of the colorless crystals, calculated based on the formula of $C_{39}H_{22}N_4O_2F_6$, are as follows:

|  | % C | % H | % N |
| --- | --- | --- | --- |
| Found | 67.41 | 3.20 | 8.11 |
| Calculated | 67.63 | 3.20 | 8.09 |

From the above results, it was confirmed that the above colorless crystals were Oxadiazole Compound No. 91 in Table 1-(10) was obtained.

APPLICATION EXAMPLE II-1

On a glass substrate provided with an indium-tin-oxide (ITO) positive electrode having a surface with a size of 3×3 mm and a thickness of 700Å, a hole-transporting layer comprising a diamine derivative of formula (37) with a thickness of 500Å, an electro-luminescent layer comprising oxadiazole compound No. 78 shown in Table 1-(10) with a thickness of 500Å, and a negative electrode comprising aluminum were successively overlaid by the vacuum deposition method under the conditions that the substrate temperature was set at room temperature, and the degree of vacuum set at about 0.7×10$^{-6}$ torr, whereby an application example of an electroluminescent device No. II-1 was prepared.

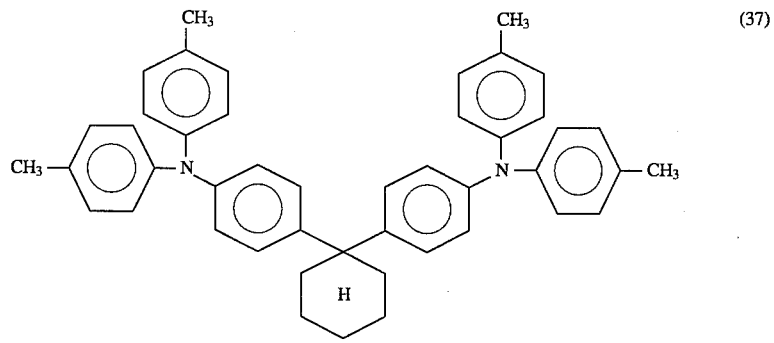

(37)

A direct electric source was connected to the electroluminescent device No. II-1 via a lead wire across the positive and negative electrodes. A clear white light emission was observed for an extended period of time by the application of a drive voltage of 25 V at a current density of 50 mA/cm$^2$, with the emission wavelength peaks at 537 nm and 407 nm, and a luminance of 400 cd/m$^2$.

After this electroluminescent device was preserved at room temperature for one month, the same clear light emission was observed.

COMPARATIVE EXAMPLE II-1

The procedure for fabrication of the application electroluminescent device No. II-1 in Application Example No. I-1 was repeated except that oxadiazole compound No. 78 employed in the electron-transporting layer in Application Example II-1 was replaced by the following compound represented by formula (38), whereby a comparative electroluminescent device No. II-1 was fabricated.

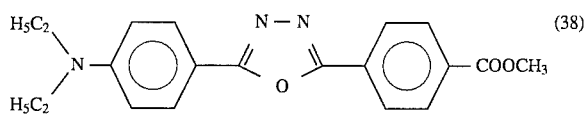

When the comparative electroluminescent device No. II-1 was caused to emit light in the same manner as in Application Example II-1, a green light emission was observed.

After the comparative electroluminescent device No. II-1 was preserved at room temperature for 1 month, the light emission was no longer observed.

EXAMPLE III-1

Synthesis of Acyl Hydrazine Compound of Formula (III-10-A) Serving as Intermediate

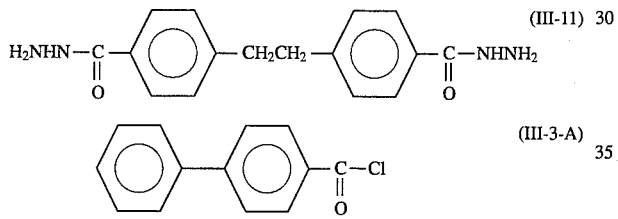

A mixture of 2.98 g of dibenzyl-4,4'-dicarboxylic acid dihydrazide of formula (III-11) and 90 ml of pyridine was stirred in a reaction flask, with the addition of 4.77 g of p-phenyl benzoic acid chloride of formula (III-3-A).

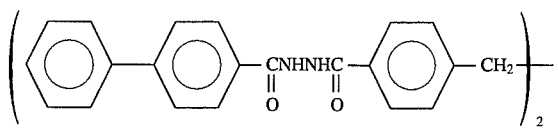

Thereafter, the thus obtained mixture was refluxed for 7 hours, and cooled to room temperature. The thus obtained reaction mixture was added to 1.5 l of water. The above mixture was filtered off and washed with water, so that a milk white crude product was obtained in a yield of 5.54 g (84%). The thus obtained crude product was recrystallized from 600 ml of N,N-dimethylformamide (DMF), whereby a pure acyl hydrazine compound of formula (III-10-A) was obtained in a yield of 4.93 g (75%).

The melting point of the above obtained acyl hydrazine compound was more than 300° C.

An infrared absorption spectrum (KBr spectrum) of the acyl hydrazine compound indicated the characteristic absorption peaks of carboxyamino group at 3250 cm$^{-1}$, 1690 cm$^{-1}$ and 1660 cm$^{-1}$.

The results of the elemental analysis of the acyl hydrazine compound, calculated based on the formula of $C_{42}H_{34}N_4O_4$, were as follows:

|  | % C | % H | % N |
|---|---|---|---|
| Found | 76.01 | 5.50 | 8.55 |
| Calculated | 76.57 | 5.21 | 8.51 |

EXAMPLES III-2 TO III-5

Synthesis of Intermediate

The procedure for synthesizing the acyl hydrazine compound of formula (III-10-A) in Example III-1 was repeated except that the p-phenyl benzoic acid chloride of formula (III-3-A) employed in Example II-1 was replaced by the respective carboxylic acid chlorides shown in Table 12, whereby intermediates represented by formulas (III-10-B) to (III-10-E) shown in Table 13 were obtained.

TABLE 12

| Ex. No. | Carboxylic Acid Chloride | Yield | Melting Point | IR (KBr Tablet) | C Found/ (Calcd.) | H Found/ (Calcd.) | N Found/ (Calcd.) | Compound No. |
|---|---|---|---|---|---|---|---|---|
| III-2 | CH₃O—⟨O⟩—COCl | 72% | >300° C. | 3250 cm⁻¹ 1690 cm⁻¹ 1660 cm⁻¹ | 67.58 (67.83) | 5.54 (5.35) | 9.81 (9.89) | (III-10-B) |
| III-3 | Cl—⟨O⟩—COCl | 73% | >300° C. | 3250 cm⁻¹ | 62.67 (62.61) | 4.42 (4.21) | 9.75 (9.74) | (III-10-C) |
| III-4 | CH₃—⟨O⟩—COCl | 73% | Not Measured | 3250 cm⁻¹ | ←— Not Analyzed —→ | | | (III-10-D) |
| III-5 | naphthyl-COCl | 65% | 284.5–285.5 | 3210 cm⁻¹ 1650 cm⁻¹ | 74.51 (75.23) | 5.54 (4.98) | 9.40 (9.23) | (III-10-E) |

TABLE 13

| Intermediate | | |
|---|---|---|
| III-10-B | $\left( CH_3O-\bigcirc-\underset{O}{\overset{\|}{C}}NHNH\underset{O}{\overset{\|}{C}}-\bigcirc-CH_2 \right)_2$ | 5 |
| III-10-C | $\left( Cl-\bigcirc-\underset{O}{\overset{\|}{C}}NHNH\underset{O}{\overset{\|}{C}}-\bigcirc-CH_2 \right)_2$ | 10 |
| III-10-D | $\left( CH_3-\bigcirc-\underset{O}{\overset{\|}{C}}NHNH\underset{O}{\overset{\|}{C}}-\bigcirc-CH_2 \right)_2$ | 15 |
| III-10-E | $\left( \bigcirc\hspace{-0.5em}\bigcirc-\underset{O}{\overset{\|}{C}}NHNH\underset{O}{\overset{\|}{C}}-\bigcirc-CH_2 \right)_2$ | 20 |

EXAMPLE III-6

Synthesis of Oxadiazole Compound No. 28 in Table 1-(4)

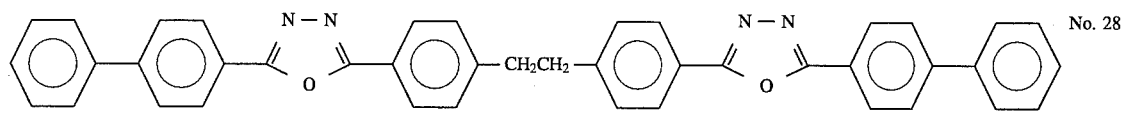
No. 28

2.0 g of acyl hydrazine of formula (III-10-A) obtained in Example III-1 was heated with stirring in the presence of 20 ml of phosphorus oxychloride serving as a dehydrating agent for 17 hours. The reaction mixture was cooled and poured into water, so that a precipitate was obtained. The precipitate was washed with water, and a crude product was obtained in a yield of 1.69 g (90%). The thus obtained crude product was recrystallized from N,N-dimethyl-formamide twice, chromatographed on a silica gel column for purification using a mixed solvent of chloroform and ethyl acetate as a developing solvent, and then further recrystallized from 1,2,4-trichlorobenzene, whereby oxadiazole compound No. 28 in Table 1-(4) was obtained in a yield of 0.19 g (10.0%).

EXAMPLE III-7

Synthesis of Oxadiazole Compound No. 29 in Table 1-(4)

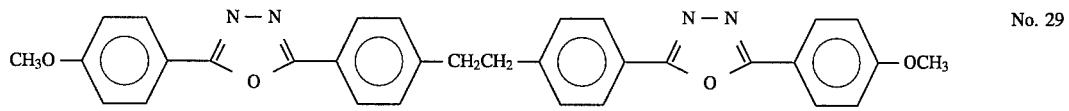
No. 29

The procedure for synthesizing of oxadiazole compound No. 28 in Example III-6 was repeated except that the acyl hydrazine compound of formula (III-10-A) employed in Example III-6 was replaced by the acyl hydrazine compound of formula (III-10-B) obtained in Example III-2, whereby oxadiazole compound No. 29 was obtained in a yield of 0.9 g (48%).

EXAMPLE III-8

Synthesis of Oxadiazole Compound No. 30 in Table 1-(4)

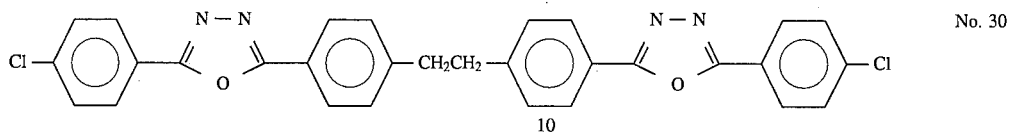

No. 30

The procedure for synthesizing oxadiazole compound No. 28 in Example III-6 was repeated except that the acyl hydrazine compound of formula (III-10-A) employed in Example III-6 was replaced by the acyl hydrazine compound of formula (III-10-C) obtained in Example III-3, whereby the oxadiazole compound No. 30 was obtained in a yield of 0.43 g (22%).

EXAMPLE III-9

Synthesis of Oxadiazole Compound No. 31 in Table 1-(4)

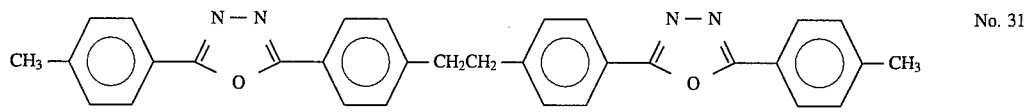

No. 31

The procedure for synthesizing of oxadiazole compound No. 28 in Example III-6 was repeated except that the acyl hydrazine compound of formula (III-10-A) employed in Example III-6 was replaced by the acyl hydrazine compound of formula (III-10-D) obtained in Example III-4, and the phosphorus oxychloride employed as a dehydrating agent in Example III-6 was replaced by polyphosphoric acid, whereby a crude oxadiazole compound was obtained. The thus obtained crude oxadiazole compound was purified by sublimation, whereby oxadiazole compound No. 31 was obtained in a yield of 0.31 g (17%).

EXAMPLE III-10

Synthesis of Oxadiazole Compound No. 32 in Table 1-(4)

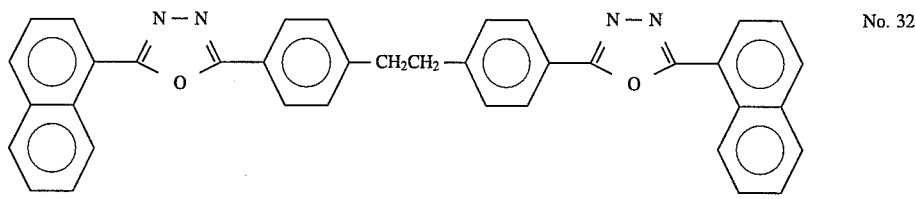

No. 32

2.47 g of the acyl hydrazine compound of formula (III-10-E) obtained in Example III-5 was refluxed in the presence of 40 ml of thionyl chloride as a dehydrating agent for 6 hours. Thereafter, the thionyl chloride was distilled away from the above mixture, and the residue was washed with water. Thus a crude product was obtained in a yield of 2.25 g (97%).

The above obtained crude product was recrystallized from N,N-dimethylformamide, and purified by sublimation, whereby oxadiazole compound No. 32 in Table 1-(4) was obtained in a yield of 0.23 g (10%).

The physical properties of the oxadiazole compounds obtained in Examples III-6 to III-10 are shown in Table 14.

TABLE 14

Figure 11:
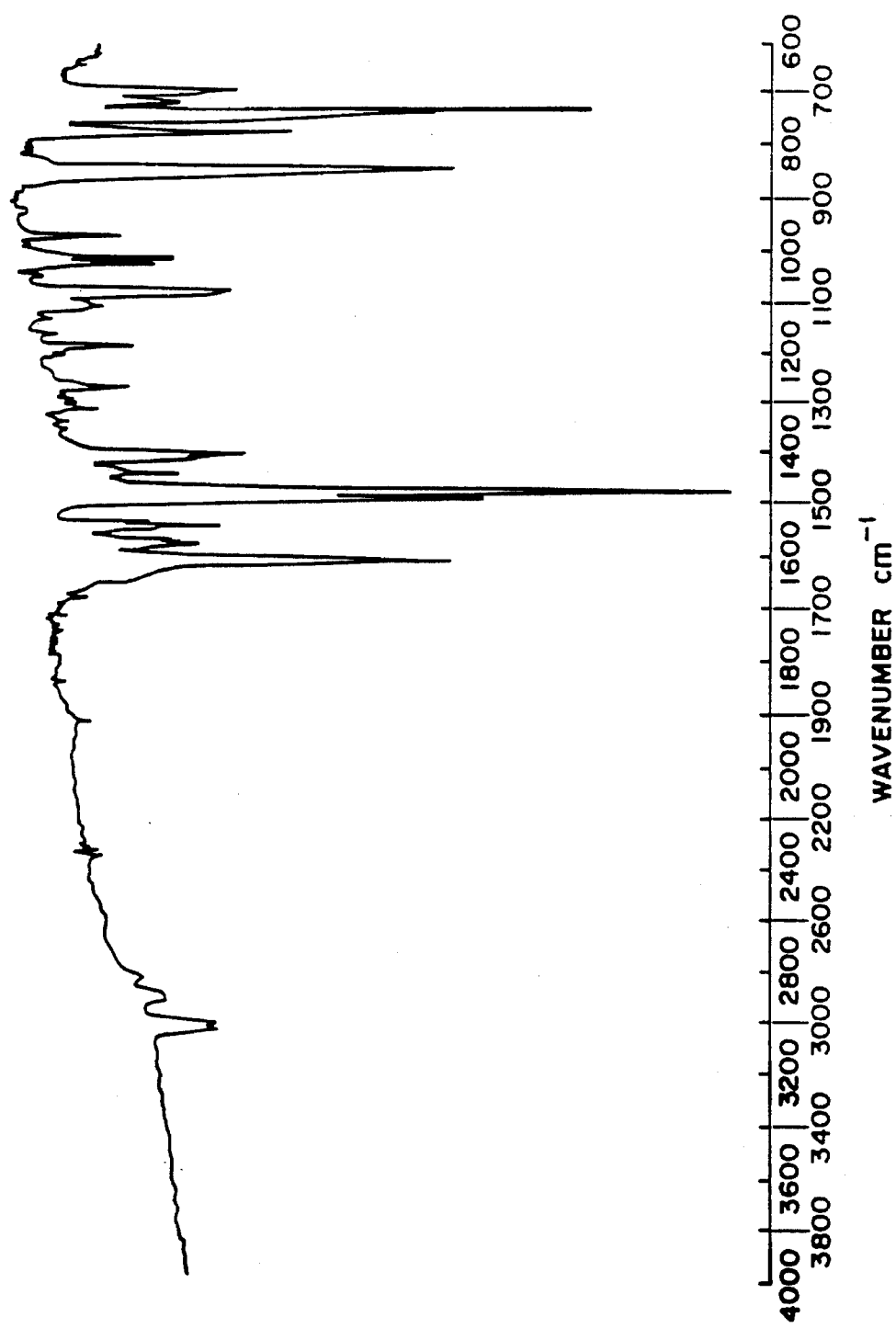
FIG. 11 is an infrared absorption spectrum (KBr tablet) of oxadiazole compound No. 28 shown in Table 1-(4)
Figure 12:
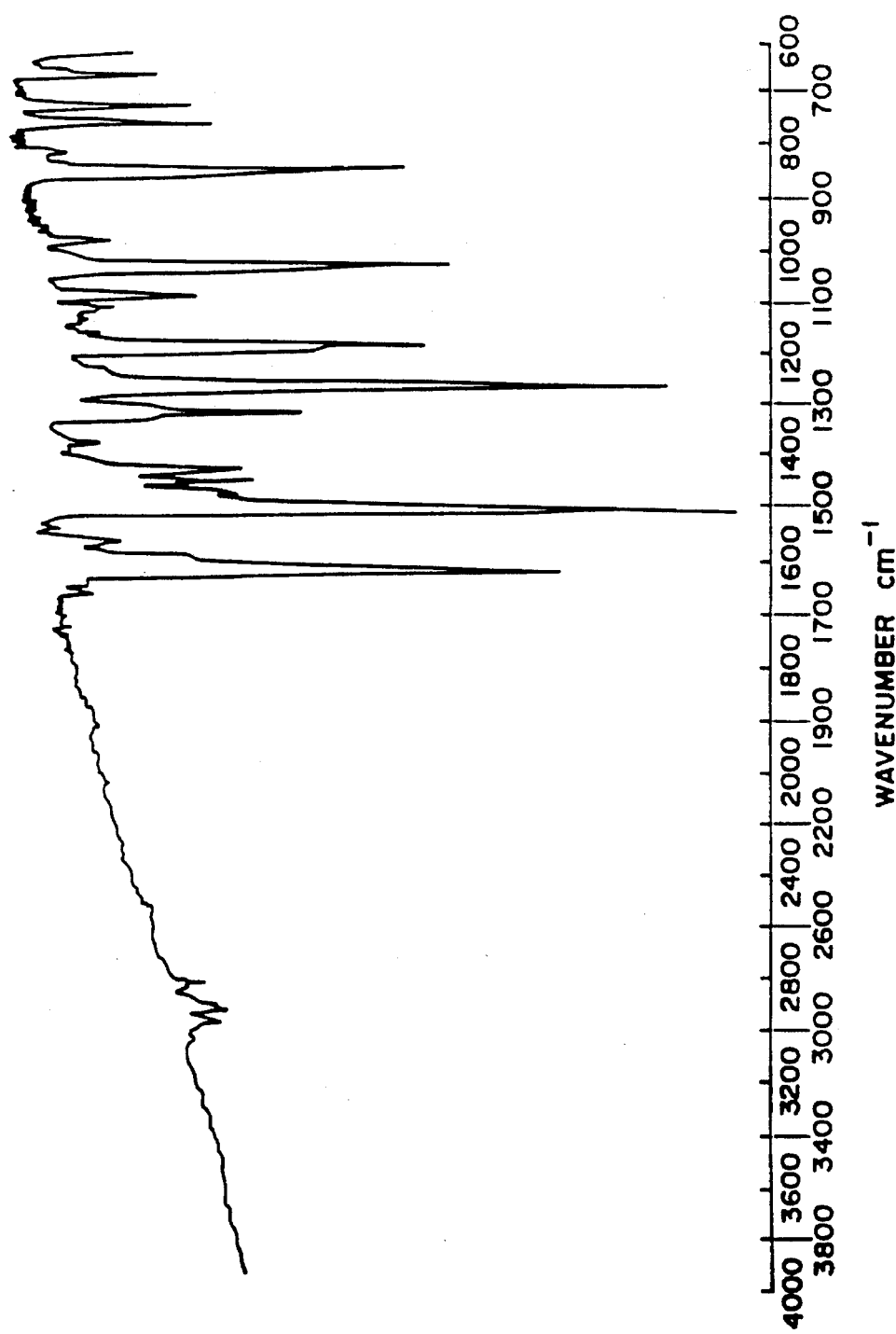
FIG. 12 is an infrared absorption spectrum (KBr tablet) of oxadiazole compound No. 29 shown in Table 1-(4)

| Ex. No. | Melting Point (°C.) | IR (KBr) | Elemental Analysis Found/(Calculated) | | |
|---|---|---|---|---|---|
| | | | % C | % H | % N |
| III-6 | 285 | FIG. 11 | 80.96 (81.00) | 5.00 (4.86) | 9.03 (9.00) |
| III-7 | 243 | FIG. 12 | 72.30 | 4.83 | 10.45 |

TABLE 14-continued

Figure 13:
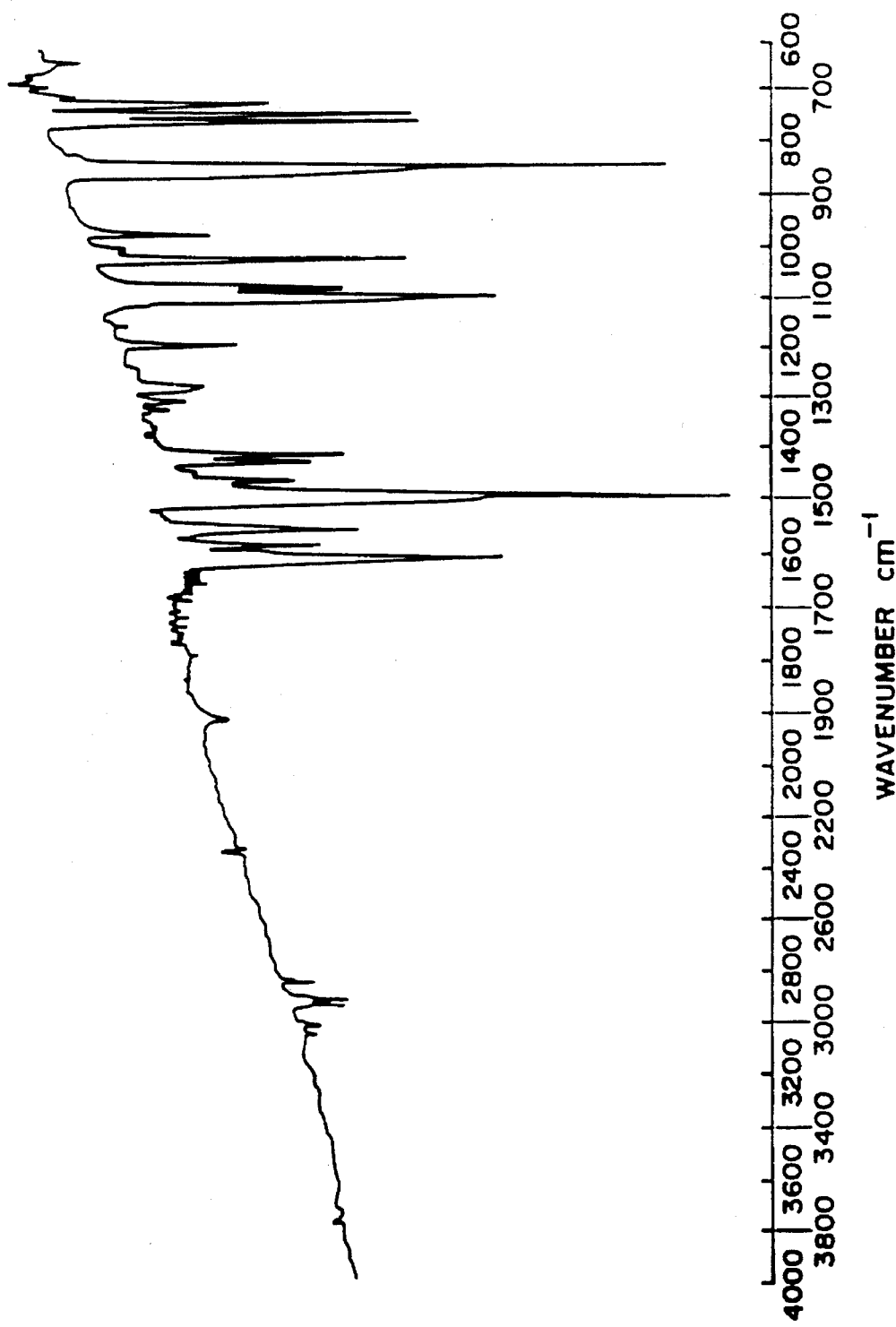
FIG. 13 is an infrared absorption spectrum (KBr tablet) of oxadiazole compound No. 30 shown in Table 1-(4)

| Ex. No. | Melting Point (°C.) | IR (KBr) | Elemental Analysis Found/(Calculated) | | |
|---|---|---|---|---|---|
| | | | % C | % H | % N |
| | | | (72.44) | (4.94) | (10.56) |
| III-8 | 288 | FIG. 13 | 66.99 | 3.46 | 10.51 |
| | | | (66.80) | (3.74) | (10.39) |
| III-9 | 258 | FIG. 14 | 77.24 | 5.05 | 11.25 |
| | | | (77.09) | (5.26) | (11.24) |
| III-10 | 283 | FIG. 15 | 79.57 | 4.33 | 9.72 |
| | | | (79.98) | (4.59) | (9.82) |

EXAMPLE III-11

Synthesis of 5,5'-(4,4'-dibenzyl) ditetrazole of formula (III-2) serving as an intermediate

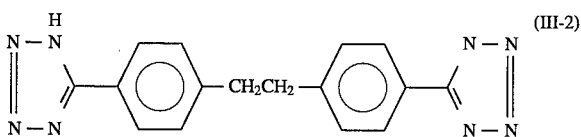
(III-2)

A mixture of 1.67 g of 4,4'-dicyano dibenzyl of formula (III-8), 1.4 g of sodium azide and 0.98 g of lithium chloride was refluxed in the presence of 50 ml of 2-methoxyethanol for 105 hours.

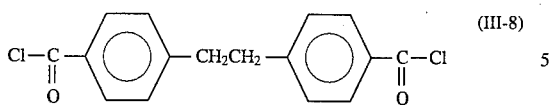

The reaction mixture was then cooled, and poured into 150 ml of ice water. The insoluble matter contained in the mixture was filtered off from the reaction mixture. To the thus obtained filtrate, about 3 ml of concentrated hydrochloric acid was added. As a result, a colorless precipitate was produced. Subsequently, the colorless precipitate was filtered off and washed with water, whereby a crude 5,5'-(4,4' dibenzyl) ditetrazole was obtained in a yield of 2.07 g (90.4%).

The crude 5,5'-(4,4' dibenzyl) ditetrazole was recrystallized from a mixed solvent of dioxane and N,N-dimethylformamide, whereby a pure 5,5'-(4,4' dibenzyl) ditetrazole of formula (III-2) was obtained in a yield of 1.78 g (77.7%).

The melting point of the above 5,5'-(4,4' dibenzyl) ditetrazole was 286.0° to 287.0° C. (decomposed with blowing).

An infrared absorption spectrum (KBr spectrum) of the 5,5'-(4,4' dibenzyl) ditetrazole indicated the characteristic absorption peaks of $\upsilon$N—H at 2800 cm$^{-1}$ to 2600 cm$^{-1}$.

EXAMPLE III-12

Synthesis of Oxadiazole Compound No. 28 in Table 1-(4)

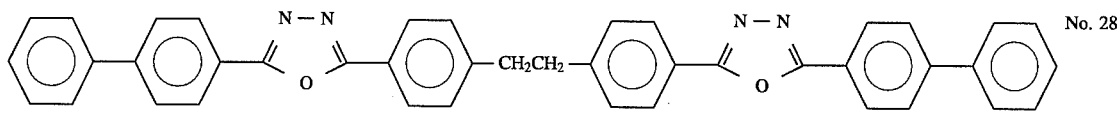

A mixture of 0.5 g of 5,5'-(4,4' dibenzyl) ditetrazole of formula (III-2) obtained in Example III-11 and 1.02 g of p-phenyl benzoic acid chloride of formula (III-3-A) was refluxed in the presence of pyridine for 13 hours. The thus obtained reaction mixture was cooled to room temperature and then poured into 150 ml of water. As a result, a precipitate was formed.

The precipitate was filtered off, washed with water, whereby oxadiazole compound No. 28 was obtained in a yield of 0.9 g (92%).

It was unnecessary to purify the above oxadiazole compound No. 28 because almost no impurities were contained in the product.

APPLICATION EXAMPLE III-1

On a glass substrate 1 provided with an indium-tin-oxide (ITO) positive electrode 2 having a surface resistivity of 20 Ω/, an electroluminescent layer 3a comprising the stilbene derivative of formula (5) shown in Table 4 with a thickness of 500Å, an electron-transporting layer 3b comprising the oxadiazole compound of formula (III-1-A) with a thickness of 500Å, and a negative electrode 4 comprising a magnesium-silver alloy with an atomic ratio of 10:1, with a thickness of 2000Å, were successively overlaid by the vacuum deposition method, whereby an application example of an electroluminescent device No. III-1 having the structure as shown in FIG. 3 was fabricated.

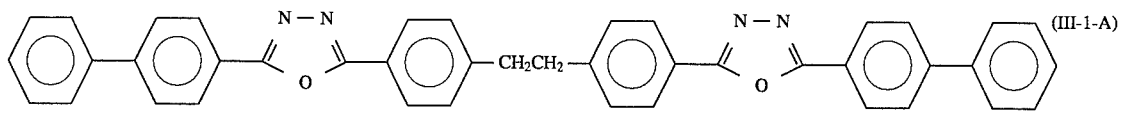

The thus fabricated application electroluminescent device No. III-1 emitted a clear blue light by the application of a drive voltage of 20 V or less. This electroluminescent device little deteriorated with time.

APPLICATION EXAMPLES III-2 TO III-5

The procedure for fabrication of the electro-luminescent device No. III-1 in Application Example III-1 was repeated except that the oxadiazole compound of formula (III-1-A) employed in the electron-transporting layer in Application Example III-1 was replaced by oxadiazole compounds Nos. 28 to 31, respectively, whereby electroluminescent devices Nos. III-2 to III-5 were fabricated.

Each of the thus fabricated electroluminescent devices Nos. III-2 to III-5 emitted a clear blue light by the application of a drive voltage of 20 V or less. These electroluminescent devices little deteriorated with time and stable in the same manner as that fabricated in Application Example III-1.

As is obvious from the above Examples, the electroluminescent device according to the present invention comprising any of the oxadiazole compounds (I), (II), (III), (IV), (V), (VI) and (VII) in the organic compound layer emits light with high luminance for an extended period of time even by the application of a low drive voltage, and produces various kinds of colors.

Moreover, the above-mentioned oxadiazole compounds have excellent film-forming properties and are stable with time, so that there is the advantage that the electroluminescent device comprising the oxadiazole compound can be obtained by a simple method.

The novel oxadiazole derivative of formula (VII) and the novel oxadiazole compound of formula (III-1) according to the present invention can be effectively utilized as a component for the electroluminescent device capable of emitting blue light with high luminance and stability since they are excellent in film-forming properties, fluorescent properties, and electron-transporting performance.

Particularly when the electroluminescent device as shown FIGS. 3 or 4 comprises the oxadiazole compound of formula (III-1) as a component for the electron-transporting layer, light for any color such as blue can be produced, and the electroluminescent device with excellent durability which emits light with high luminance can be obtained.

Furthermore, the oxadiazole compound of formula (III-1) which is useful as a constituent material for the electroluminescent device can be easily synthesized in accordance with the method for producing the oxadiazole compound (III-1) of the present invention.

What is claimed is:

1. A novel oxadiazole compound represented by formula (III-1):

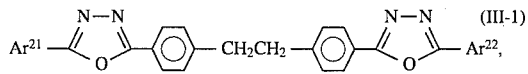

wherein $Ar^{21}$ and $Ar^{22}$ each is selected from the group consisting of naphthyl group, anthryl group, phenanthryl group, biphenylyl group and an aromatic heterocyclic group.

2. The novel oxadiazole compound as claimed in claim 1, wherein $Ar^{21}$ and $Ar^{22}$ are the same.

3. The novel oxadiazole compound as claimed in claim 1, wherein said $Ar^{21}$ and $Ar^{22}$ is selected from the group consisting of naphthyl group, anthryl group, pyridyl group, phenanthryl group and biphenylyl group.

* * * * *

UNITED STATES PATENT AND TRADEMARK OFFICE
CERTIFICATE OF CORRECTION

PATENT NO. : 5,610,309

DATED : March 11, 1997

INVENTOR(S) : Masafumi OHTA, et al.

It is certified that error appears in the above-identified patent and that said Letters Patent is hereby corrected as shown below:

Column 1, line 23, insert "also" after "invention".

Column 3, line 26, "devices for organic" should read --devices or organic--.

Figure 14:
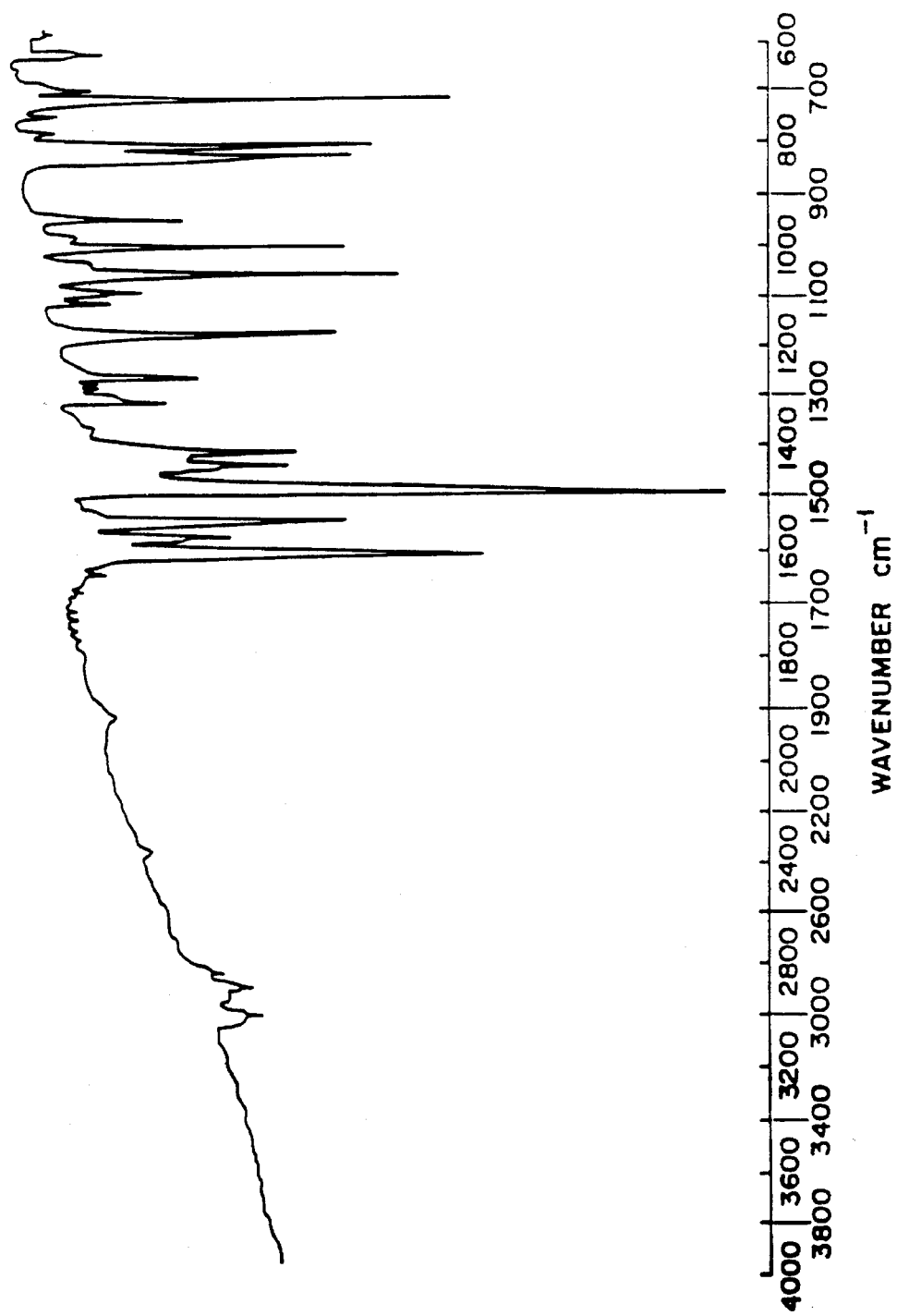
FIG. 14 is an infrared absorption spectrum (KBr tablet) of oxadiazole compound No. 31 shown in Table 1-(4)
Figure 15:
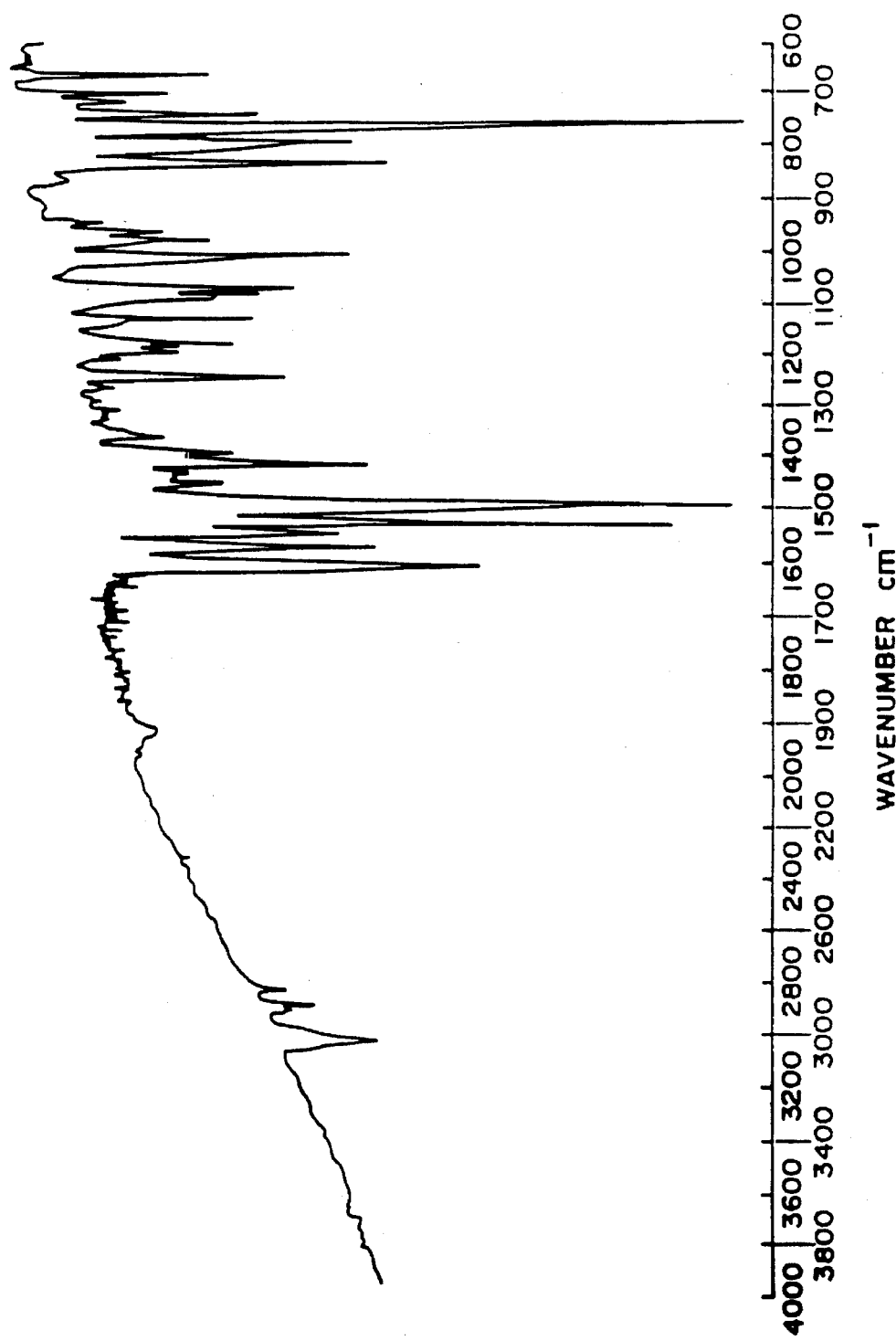

Column 8, line 34, "FIG. 14" should read --FIG. 15--.

Column 11, line 40 "from a ring" should read --form a ring--.

Column 13, line 1, "an sulfonyl" should read --a sulfonyl--.

Column 41, line 24, "2 and 4," should read --2 and 4.--.

Column 46, lines 45 and 46, "resistivity of 20Ω/," should read --resistivity of 20 Ω/□,--.

Column 49, line 35, "resistivity of 20Ω/58," should read --resistivity of 20 Ω/□,--.

UNITED STATES PATENT AND TRADEMARK OFFICE
CERTIFICATE OF CORRECTION

PATENT NO. : 5,610,309
DATED : March 11, 1997
INVENTOR(S) : Masafumi OHTA, et al.

It is certified that error appears in the above-identified patent and that said Letters Patent is hereby corrected as shown below:

Column 55, line 5, "produce" should read --product--;
    line 48, "p-phenyl benzoly chloride"
should read --p-phenyl benzoyl chloride--.

Column 62, line 19, "this crystals" should read
    --these crystals--.

Column 64, line 65, "9.14 g (71.4%." should read
    --9.14 g (71.4%).--.

Column 74, line 1, "20Ω/," should read --20 Ω/□,--.

Signed and Sealed this

Nineteenth Day of May, 1998

Attest:

BRUCE LEHMAN

Attesting Officer     Commissioner of Patents and Trademarks